(12) United States Patent
Fink et al.

(10) Patent No.: US 7,652,046 B2
(45) Date of Patent: Jan. 26, 2010

(54) SUBSTITUTED THIENOPYRROLE CARBOXYLIC ACID AMIDES, PYRROLOTHIAZOLE CARBOXYLIC ACID AMIDES, AND RELATED ANALOGS AS INHIBITORS OF CASEIN KINASE I

(75) Inventors: David Marc Fink, Lebanon, NJ (US); Yulin Chiang, Convent Station, NJ (US); Nicola Dawn Collar, Hoboken, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 3 days.

(21) Appl. No.: 12/125,450

(22) Filed: May 22, 2008

(65) Prior Publication Data

US 2008/0227822 A1    Sep. 18, 2008

Related U.S. Application Data

(63) Continuation of application No. 11/674,349, filed on Feb. 13, 2007, now Pat. No. 7,393,867, which is a continuation of application No. PCT/US2005/029383, filed on Aug. 18, 2005.

(60) Provisional application No. 60/603,647, filed on Aug. 19, 2004.

(51) Int. Cl.
*A61K 31/429*   (2006.01)
*A61K 31/407*   (2006.01)

(52) U.S. Cl. .................... 514/367; 514/418

(58) Field of Classification Search ............ 514/367, 514/418
See application file for complete search history.

(56) References Cited

U.S. PATENT DOCUMENTS 6,555,328 B1    4/2003  Keesler et al.

FOREIGN PATENT DOCUMENTS

WO    WO 2005/061498    7/2005

OTHER PUBLICATIONS

"Isomer." Retrieved online via the internet [Mar. 6, 2009] http://en.wikipedia.org/wiki/Isomer.*
"Parkinson's Disease." Retrieved online via the internet [Mar. 6, 2009] www.nlm.nlh.gov/medlineplus/parkinsonsdisease.html.*

Mashhoon, N., et. al., Crystal Structure of a Conformation-Selective Casein Kinase-1 Inhibitor, J. Biol. Chem. vol. 275, No. 26, (2000) pp. 20052-20060.
Meggio, F., et. al., Ribofuranosyl-benzimidazole derivatives as inhibitors of casein kinase-2 and casein kinase-1 , European Journal of Niochemistry vol. 187, No. 1, (1990) pp. 89-94.
Ning, K., et. al., Circadian Regulation of GABAA Receptor Function by CKI-Epsilon-CKI-delta in the rat Suprachiasmatic Nuclei, Nature Neuroscience, Nature America, vol. 7, No. 5, (2004).
6-phenylsulfanyl-4H-thieno[3,2-b]pyrrole-5-carboxylic acid ethyl esters, Database Beilstein XP002366005 Database Accession Nos. 5099280, 5108767, 5110689 (BRN's). & J. Chem. Soc. Perkin Trans. 1, 1986, pp. 501-506.
Gairns, R. S., et. al., Photochemical Conversion of 3-Azido-2-Vinylthiophenes into Thienopyrroles and of 2-Azidostyrenes into Indoles. High Migratory Aptitutde of Sulphur Substituents, J. Chem. Soc. Perkins Trans. I, pp. 501-506 (1986).

* cited by examiner

*Primary Examiner*—Kamal A Saeed
*Assistant Examiner*—Samantha L Shterengarts
(74) *Attorney, Agent, or Firm*—Balaram Gupta

(57) ABSTRACT

The present invention comprises methods for the treatment of central nervous system diseases and disorders including mood disorders and sleep disorders through the administration of compounds of formula (I) and formula (II)

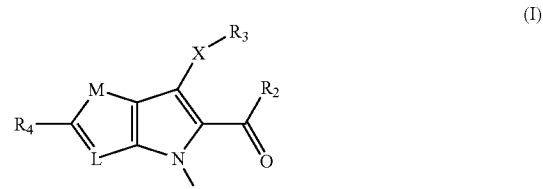

(I)

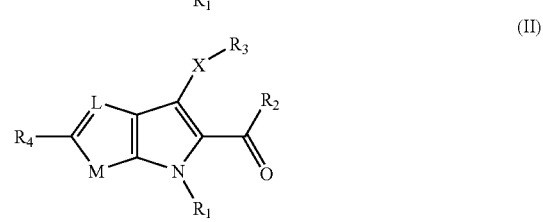

(II)

which are useful as inhibitors of human casein kinase Iε. Pharmaceutical compositions comprising compounds of formula (I) or formula (II) as well as methods for their preparation are also disclosed and claimed.

5 Claims, No Drawings

SUBSTITUTED THIENOPYRROLE CARBOXYLIC ACID AMIDES, PYRROLOTHIAZOLE CARBOXYLIC ACID AMIDES, AND RELATED ANALOGS AS INHIBITORS OF CASEIN KINASE I

CROSS-REFERENCE TO RELATED APPLICATIONS

This application is a continuation Of U.S. Ser. No. 11/674,349 filed on Feb. 13, 2007 which is a continuation of International Patent Application No. PCT/EP2005/029383 filed on Aug. 18, 2005 which is incorporated herein by reference in its entirety which also claims the benefit of priority of U.S. Provisional Appln. Ser. No. 60/603,347 filed on Aug. 19, 2004.

FIELD OF THE INVENTION

This invention relates generally to methods for the treatment and/or prevention of diseases and disorders associated with the central nervous system, more particularly, those involving regulation of the human clock protein Period (hPER). More specifically, the present invention relates to methods for the treatment and/or prevention of diseases and disorders associated with the central nervous system through the administration of a series of substituted 4H-thieno[3,2-b]pyrrole-5-carboxylic acid amides and related analogs, and to methods of making the compounds which are inhibitors of human casein kinase I$\epsilon$ phosphorylation of the human clock protein Period (hPER). More particularly, the present invention relates to a series of substituted 4H-thieno[3,2-b]pyrrole-5-carboxylic acid amides, 4H-pyrrolo[2,3-d]thiazole-5-carboxylic acid amides, 6H-thieno[2,3-b]pyrrole-5-carboxylic acid amides, 4H-pyrrolo[3,2-d]thiazole-5-carboxylic acid amides and related analogs and their use in the treatment of the above-referenced disorders. Most specifically the invention relates to the use of 3-arylthio-substituted and 3-heterocyclethio-substituted 4H-thieno[3,2-b]pyrrole-5-carboxylic acid amides, 4H-pyrrolo[2,3-d]thiazole-5-carboxylic acid amides, 6H-thieno[2,3-b]pyrrole-5-carboxylic acid amides, 4H-pyrrolo[3,2-d]thiazole-5-carboxylic acid amides, and related analogs, and to methods of making the compounds of the invention.

BACKGROUND OF THE INVENTION

Rhythmic variations in behavior are displayed by many organisms, ranging from single cells to man. When the rhythm persists under constant conditions, and has a period of about one day, depending little on temperature, the rhythm is called "circadian" (Konopka, R. J. and Benzer, S. (1971) Proc. Nat. Acad. Sci. USA 68, 2112-2116).

Circadian rhythms are generated by endogenous biological pacemakers (circadian clocks) and are present in most living organisms including humans, fungi, insects and bacteria (Dunlap, J. C. (1999) Cell 96, 271-290; Hastings, J. W. et al. Circadian Rhythms, The Physiology of Biological Timing. In: Prosser, C. L. ed. Neural and Integrative Animal Physiology, New York: Wiley-Liss (1991) 435-546; Allada, R. et al. (1998) Cell 93, 791-804; Kondo et al. (1994) Science 266, 1233-1236; Crosthwaite, S. K. et al. (1997) Science 276, 763-769; Shearman, L. P. et al. (1997) Neuron, 19, 1261-1269). Circadian rhythms are self-sustaining and constant even under conditions of total darkness, but can be synchronized (entrained) to a new day/night regime by environmental signals such as light and temperature cycles (Pittendrigh, C. S. (1993) Annu. Rev. Physiol., 55, 16-54; Takahashi, J. S. (1995) Annu. Rev. Neurosci. 18, 531-553; Albrecht, U. et al. (1997) Cell, 91, 1055-1064). Circadian clocks are essential for maintaining biological rhythms and regulate a variety of circadian behaviors such as daily fluctuations in behavior, food intake and the sleep/wake cycle, as well as physiological changes such as hormone secretion and fluctuations in body temperature (Hastings, M. (1997) Trends Neurosci. 20, 459-464; Reppert, S. M. and Weaver, D. R. (1997) Cell 89, 487-490).

Genetic and molecular studies in the fruit fly *Drosophila melanogaster* led to elucidation of some of the genes involved in circadian rhythmicity. These studies led to recognition of a pathway that is closely auto-regulated and comprised of a transcription/translation-based negative feed back loop (Dunlap, J. C. (1999) Cell, 96, 271-290; Dunlap, J. C. (1996) Annu. Rev. Genet. 30, 579-601; Hall, J. C. (1996) Neuron, 17, 799-802). The core elements of the circadian oscillator in *Drosophila* consists of two stimulatory proteins dCLOCK/dBMAL (CYCLE) and two inhibitory proteins dPERIOD (dPER) and dTIMELESS (dTIM). dCLOCK and dBMAL heterodimerize forming the transcription factor dCLOCK/dBMAL that promotes expression of two genes termed *Drosophila* Period (dper) and *Drosophila* Timeless (dtim). Ultimately the mRNAs from these genes are transcribed to afford the proteins dPER and dTIM, respectively. For several hours the protein products dPER and dTIM are synthesized and phosphorylated in the cytoplasm, reach a critical level, and form heterodimers that are translocated into the nucleus. Once in the nucleus dPER and dTIM function as negative regulators of their own transcription, accumulation of dPER and dTIM declines, and activation of dper and dtim by dCLOCK/dBMAL starts again (Zylka, M. J. et al. (1998) Neuron 20, 1103-1110; Lowrey, P. L. et al. (2000) 288, 483-491). The dper gene has been shown to be a necessary element in controlling circadian rhythms in adult eclosion (the emergence of the adult fly from the pupa) behavior and locomotor activity (Konopka, R. J., & Benzer, S. (1971) Proc. Natl. Acad. Sci. USA, 68, 2112-2116). Missense mutations of the per gene can either shorten (per$^S$) or lengthen (per$^L$) the period of circadian rhythms, while nonsense mutations (per$^o$) cause arrhythmicity in their behaviors (Hall, J. C. (1995) Trends Neurosci. 18, 230-240).

In mammals, the suprachiasmatic nuclei (SCN) of the anterior hypothalamus are the site of a master biological clock (for review see Panda et al, (2002) Nature 417, 329-335; Reppert, S. M. and Weaver, D. R. (1997) Cell, 89, 487-490). The SCN clock is entrained to the 24 hour day by the daily light-dark cycle, with light acting through both direct and indirect retina-to-SCN pathways (Klein, D. C. et al. (1991) Suprachiasmatic Nuclei The Mind's Clock, Oxford University Press, New York). In the SCN of rodents, three Per genes have been identified and cloned, and are designated as mouse Per1 (mPer1), mPer2 and mPer3. The protein products of these mammalian genes (mPER1, mPER2, mPER3) share several regions of homology to each other, and each mammalian Per gene encodes a protein with a protein dimerization domain designated as PAS (PAS is an acronym for the first three proteins PER, ARNT and SIM found to share this functionally important dimerization domain) that is highly homologous to the PAS domain of insect PER. All Per messenger RNAs (mRNAs) and protein levels oscillate during the circadian day and are intimately involved in both positive and negative regulation of the biological clock, but only mPER1 and mPER2 oscillate in response to light (Zylka, M. J. et al. (1998) Neuron 20, 1103-1110; Albrecht, U. et al., (1997) Cell 91, 1055-1064; Shearman, L. P. et al. (1997) Neuron 19, 1261-1269). The mammalian homolog of the *Drosophila* tim gene was cloned and designated as mTim. However, there was no evidence for mPER-mTIM interactions analogous to those observed in *Drosophila*, and it was suggested that PER-PER interactions may have replaced the function of PER-TIM dimers in the molecular workings of the mammalian circadian clock (Zylka, M. J. et al., (1998) Neuron 21, 1115-1122). Another possibility is that rhythms in PER1 and PER2 form negative feedback loops that regulate the transcriptional activity of the Clock protein (via their PAS domains), which, in turn, drives expression of either or both Per genes (Shearman, L. P. et al. (1997) Neuron 19, 1261-1269).

Understanding the roles of the three mPer genes in the mammalian clockwork has been the subject of much investigation. The structural homology of the mPER proteins to dPER led to the expectation that the mPER proteins would function as negative elements in the mammalian feedback loop. PER1 is believed to be involved in the negative regulation of its own transcription in the feedback loop, but recent evidence points to it being involved in the input pathway (Hastings, M. H. et al. (1999) Proc. Natl. Acad. Sci. USA 26, 15211-15216). PER2 is the most well characterized protein, and mPER2 mutant mice ($mPer2^{Brdm1}$), lacking 87 residues at the carboxyl portion of the PAS dimerization domain, have a shortened circadian cycle in normal light-dark settings, but show arrhythmicity in complete darkness. The mutation also diminishes the oscillating expression of both mPer1 and mPer2 in the SCN, indicating that mPer2 may regulate mPer1 in vivo (Zheng, B. et al. (1999) Nature 400, 169-173). PER2 has been shown to have a dual function in the regulation of the "gears" of the central clock (Shearman, L. P. et al. (2000) Science 288, 1013-1018). In that study, PER2 was shown to bind to cryptochrome (CRY) proteins and translocate to the nucleus where CRY negatively regulated transcription driven by the CLOCK and BMAL1 positive transcriptional complexes. Upon nuclear entry, PER2 initiated the positive arm of the clock by positively regulating BMAL1 transcription by a yet unidentified mechanism. The function of PER3 is poorly understood; however, in mPer3 knockout mice a subtle effect on circadian activity is observed, and therefore PER3 has been suggested to be involved in the circadian controlled output pathways (Shearman, L. P. et al. (2000) Mol. Cell. Biol. 17, 6269-6275). It has been reported that mPER proteins interact with each other and that mPER3 can serve as a carrier of mPER1 and mPER2 to bring them into the nucleus which is critical for the generation of circadian signals in the SCN (Kume, K. et al. (1999) Cell 98, 193-205; Takano, A. et al. (2000), FEBS Letters, 477, 106-112).

Phosphorylation of the components of the circadian clock has been postulated to regulate the duration of the cycle. The first genetic evidence that a specific protein kinase regulates the *Drosophila* circadian rhythm was the discovery of the novel gene doubletime (dbt), encoding a protein serine/threonine kinase (Price J. L. et al. (1998) Cell 94, 83-95; Kloss B. et al. (1998) Cell 94, 97-107). Missense mutations in the dbt result in an altered circadian rhythm. Null alleles of dbt result in hypophosphorylation of dPER and arrhythmia.

The mammalian kinases most closely related to DBT are casein kinase Iε (CKIε and casein kinase Iδ (CKIδ. Both kinases have been shown to bind to mPER1, and several studies have shown that CKIε phosphorylates both mouse and human PER1 (Price J. L. et al. (1998) Cell 94, 83-95; Kloss B. et al. (1998) Cell 94, 97-107). In a study with human embryonic kidney 293T cells co-transfected with wild-type hCKIε hPER1 showed a significant increase in phosphorylation (evidenced by a shift in molecular mass). In this study, the phosphorylated hPER1 had a half-life of approximately twelve hours whereas unphosphorylated hPER1 remained stable in the cell for more that 24 hours, suggesting phosphorylation of hPER1 leads to a decrease in protein stability (Kessler, G. A. et al. (2000) NeuroReport, 11, 951-955). Another study also showed the consequence of PER1 phosphorylation by hCKIε includes both cytoplasmic retention and protein instability (Vielhaber, E. et al. (2000) Mol. Cell. Biol. 13, 4888-4899; Takano, A. et al. (2000) FEBS Letters 477, 106-112).

There has been no biochemical reason to choose between CKIε or CKIδ as a potential regulator in mammals until Lowery et al. [(2000) Science 288, 483-491] found that in the Syrian Golden hamster, semidominant mutations in CKIε (tau mutation, Ralph, M. R. and Menaker, M. (1988) Science 241, 1225-1227) caused a shortened circadian day in both heterozygous (22 h) and homozygous (20 h) animals. In this instance, reduced levels of CKIε activity resulted in less PER phosphorylation with presumably higher levels of cytoplasmic PER protein leading to enhanced nuclear entry and altered circadian cycles. More recently, it has been suggested that CKIδ may also be involved in regulating circadian rhythmicity by post-translation modification of mammalian clock proteins hPER1 and hPER2 [Camacho, F. et al., (2001) FEBS Letters 489(2,3), 159-165]. Thus, inhibitors, including small molecule inhibitors, of mammalian or human CKIε and/or CKIδ provide a novel means to phase shift or reset the circadian clock. As discussed below, the alteration of circadian rhythm may find utility for the treatment of sleep or mood disorders.

U.S. Pat. No. 6,555,328 B1 discloses screening methods in cells to identify compounds that alter circadian rhythms based on a test compound altering the ability of human casein kinase 1ε and/or human casein kinase 1δ to phosphorylate the human clock proteins hPER1, hPER2 and hPER3. For example, HEK293T cells are co-transfected with hCKIε and Per1 or Per2. For the purpose of evaluating the relevancy of CKIε inhibition and CKIε inhibitors to circadian biology, a high-throughput cellular assay ($33^{rd}$ Annual Meeting, Soc. for Neurosci., Nov. 8-12, 2003, Abstract numbers 284.1, 284.2, and 284.3) was developed in which circadian rhythm could be monitored in a routine manner. The assay consists of Rat-1 fibroblasts stably expressing a Mper1-luc construct, thus enabling the determination of the rhythmic activation of the Mper1 promoter in living cells by repeatedly estimating luciferase activity by monitoring light-output over several days. The repeated measure format of the assay permits accurate and reproducible assessment of the concentration-dependent effects of CKIε inhibitors on circadian rhythm and provides the nexus for relating CKIε inhibition to circadian period alteration.

Sleep disorders have been classified into four major categories that include primary sleep disorders (dyssomnias and parasomnias), sleep disorders associated with medical/psychiatric disorders and a category of proposed sleep disorders for sleep disorders that cannot be classified due to insufficient data. Primary sleep disorders are thought to arise from abnormalities in the intrinsic systems responsible for sleep-wake generation (homeostatic system) or timing (circadian system). Dyssomnias are disorders in initiating or maintaining sleep and include primary insomnia, hypersomnia (excessive sleepiness), narcolepsy, breathing-related sleep disorder, circadian rhythm sleep disorder, and dyssomnias not otherwise specified. Primary insomnia is characterized by the persistence (>1 month) in difficulty of initiating and maintaining sleep or of non-restorative sleep. Difficulties in sleeping associated with primary insomnia leads to significant distress or impairment, including daytime irritability, loss of attention and concentration, fatigue and malaise, and deterioration of mood and motivation. Circadian rhythm sleep disorders include jet lag syndrome, shift work sleep disorder, advanced sleep phase syndrome and delayed sleep phase syndrome (J. Wagner, M. L. Wagner and W. A. Hening, Annals of Pharmacotherapy (1998) 32, 680-691). Individuals in a forced sleep paradigm demonstrate a greater wakefulness, as a percentage of sleep time, at certain periods of circadian day (Dijk and Lockley, J. Appl. Physiol. (2002) 92, 852-862). It has been generally accepted that with age there is an advance in our circadian rhythm for sleep and often results in less quality sleep (Am J Physiol Endocrinol Metab. (2002) 282, E297-E303). Thus, sleep occurring out of circadian phase may suffer in qualitative and quantitative terms, as further exemplified by alterations in sleep with shift work and jet lag. Disturbance of the human circadian clock can cause sleep disorders and agents that modulate circadian rhythmicity, such as an inhibitor of CKIε and/or CKIδ, may be useful for the treatment of sleep disorders, and particularly circadian rhythm sleep disorders.

Mood disorders are divided into depressive disorders ("unipolar depression"), bipolar disorders, and two disorders based on etiology that include mood disorder due to a general medical condition and substance-induced mood disorder. Depressive disorders are subclassified as major depressive disorder, dysthymic disorder and depressive disorder not otherwise specified. Bipolar disorders are subclassified as bipolar I disorder and bipolar II disorder. It has been observed that the specifier "seasonal pattern" can be applied to major depressive disorders that are recurrent and to the pattern of major depressive episodes in bipolar I disorder and bipolar II disorder. Prominent anergy, hypersomnia, overeating, weight gain, and a craving for carbohydrates often characterize major depressive episodes that occur in a seasonal pattern. It is unclear whether a seasonal pattern is more likely in major depressive disorder that is recurrent or in bipolar disorders. However, within the bipolar disorders, a seasonal pattern appears to be more likely in bipolar II disorder than in bipolar I disorder. In some individuals the onset of manic or hypomanic episodes may also be linked to a particular season. The winter-type seasonal pattern appears to vary with latitude, age and sex. Prevalence increases with higher latitudes, younger persons are at higher risk for winter depressive episodes, and females comprise 60% to 90% of persons with seasonal pattern. Seasonal affective disorder (SAD), a term commonly used in the literature, is a subtype of mood disorder that in the Diagnostic and Statistical Manual of Mental Disorders IV (DSM-IV) (American Psychiatric Association: "Diagnostic and Statistical Manual of Mental Disorders", Fourth Edition, Text Revision. Washington, D.C., American Psychiatric Association, 2000) is denoted by the term "with seasonal pattern" when describing a seasonal pattern of major depressive episodes in bipolar I disorder, bipolar II disorder or recurrent major depressive disorder (E. M. Tam et al., Can. J. Psychiatry (1995) 40, 457-466). The characteristics and diagnoses of depressive disorders, major depressive disorder, major depressive episode, bipolar I disorder, bipolar II disorder and seasonal effects are described in DSM-IV, Patients suffering from major depressive disorders, including SAD that is characterized by recurrent depressive episodes typically in winter, have been shown to be positively responsive to light therapy (Kripke, Journal of Affective Disorders (1998) 49 (2), 109-117). The success of bright light treatment for patients with SAD and major depression resulted in the proposal of several hypotheses to explain the underlying mechanism of action for the therapeutic effect of light. These hypotheses included the "circadian rhythm hypothesis" that suggests the antidepressant effect of bright light could be associated with phase-shifting the circadian pacemaker relative to sleep (E. M. Tam et al., Can. J. Psychiatry (1995) 40, 457-466). In support of the link between light therapy and circadian rhythm, clinically effective light therapy in major depressive disorders causes a concomitant shift in circadian phase and the clinical effectiveness of light therapy appears to depend on the phase-shifting ability of the light therapy (Czeisler et al., The Journal of Physiology (2000) 526 (Part 3), 683-694; Terman et al., Arch. Gen. Psychiatry (2001) 58, 69-75). Additionally, light-therapy has been shown to accelerate and augment the effectiveness of the pharmacological treatment of major depressive disorders (Benedetti et al., J. Clin. Psychiatry (2003) 64, 648-653). Thus, inhibition of casein kinase Iε and/or casein kinase Iδ would be expected to cause a circadian phase shift and such inhibition represents a potential clinically effective mono- or combined therapy for mood disorders.

It should be noted that sleep disturbance is a criterion symptom for many psychiatric disorders (W. V. McCall, J. Clin. Psychiatry (2001) 62 (suppl 10), 27-32). Sleep disturbances are a common feature of depressive disorders and insomnia is the sleep disturbance that is frequently reported in depression, occurring in over 90% of depressed patients (M. E. Thase, J. Clin. Psychiatry (1999) 60 (suppl 17), 28-31). Accumulating evidence supports a common pathogenesis for primary insomnia and major depressive disorder. It has been hypothesized that corticotrophin releasing factor (CRF) hyperactivity (due to genetic predisposition or possibly early stress) and stress induce a process leading to exaggerated and protracted sleep disturbances, and eventually primary insomnia. Circadian rhythmicity in CRF secretion under non-stressed conditions may play a role in the normal sleep-wake expression (G. S. Richardson and T. Roth, J. Clin Psychiatry (2001) 62 (suppl 10), 39-45). Thus, agents that modulate circadian rhythmicity, for example by inhibition of casein kinase Iε and/or casein kinase Iδ, may be useful for treatment of depressive disorders due to effects on CRF secretion.

All of the references referred to hereinabove are incorporated herein by reference in their entirety.

Thus it is an object of this invention to provide a series of substituted 4H-thieno[3,2-b]pyrrole-5-carboxylic acid amides, 4H-pyrrolo[2,3-d]thiazole-5-carboxylic acid amides, 6H-thieno[2,3-b]pyrrole-5-carboxylic acid amides, 4H-pyrrolo[3,2-d]thiazole-5-carboxylic acid amides and related analogs that are inhibitors of casein kinase Iε. This object and other objects of this invention become apparent from the detailed discussion of the invention that follows.

SUMMARY OF THE INVENTION

The present invention provides methods for the use of substituted 4H-thieno[3,2-b]pyrrole-5-carboxylic acid amides, 4H-pyrrolo[2,3-d]thiazole-5-carboxylic acid amides, 6H-thieno[2,3-b]pyrrole-5-carboxylic acid amides, 4H-pyrrolo[3,2-d]thiazole-5-carboxylic acid amides and related analogs of formula (I) and formula (II), their isomers, enantiomers, racemates and the pharmaceutically acceptable salts thereof, as inhibitors of human casein kinase Iε activity, and methods of using the compounds of formula (I) and formula (II) as pharmaceutical agents for the treatment of diseases and disorders of the central nervous system, such as for example mood disorders including major depressive disorder, bipolar I disorder and bipolar II disorder, and sleep disorders including circadian rhythm sleep disorders such as for example shift work sleep disorder, jet lag syndrome, advanced sleep phase syndrome and delayed sleep phase syndrome. The present invention also provides methods for making the compounds of formula (I) and formula (II) of the invention.

Accordingly, a broad embodiment of the invention is directed to methods for the therapeutical use of compounds of formula (I) or formula (II):

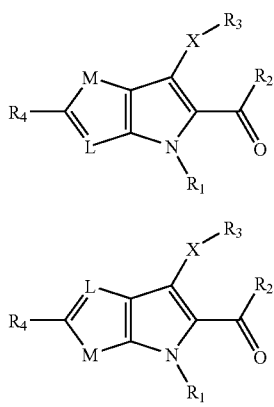

wherein

X is S or S(O)$_n$;

R$_1$ is H or C$_1$-C$_6$alkyl;

R$_2$ is NR$_5$R$_6$;

R$_3$ is aryl or heterocycle;

R$_4$ is H, C$_1$-C$_6$alkyl, C$_2$-C$_6$alkenyl, C$_2$-C$_6$alkynyl, aryl-(C$_1$-C$_6$alkyl), heterocycle-(C$_1$-C$_6$alkyl), C$_1$-C$_6$alkoxy, aryl-(C$_1$-C$_6$alkoxy), heterocycle-(C$_1$-C$_6$alkoxy), CF$_3$, halogen, SH, C$_{1-6}$alkylthio, aryl-(C$_1$-C$_6$alkylthio), heterocycle-(C$_1$-C$_6$alkylthio), NO$_2$, NH$_2$, NR$_5$R$_6$, aryl-(C$_1$-C$_6$alkylamino), heterocycle-(C$_1$-C$_6$alkylamino), or XR$_3$ wherein X and R$_3$ are as defined above;

R$_5$ is H or C$_1$-C$_6$alkyl;

R$_6$ is H or C$_1$-C$_6$alkyl;

L is N or CR$_7$ wherein R$_7$ is H or C$_1$-C$_6$alkyl;

M is S, O or NR$_8$ wherein R$_8$ is H, C$_1$-C$_6$alkyl, aryl-(C$_1$-C$_6$alkyl), heterocycle-(C$_1$-C$_6$alkyl) or acyl;

n is 1 or 2; or their isomers, enantiomers, racemates and the pharmaceutically acceptable salts thereof.

Another embodiment of the present invention relates to a method for inhibiting casein kinase Iε activity in a patient comprising administering to said patient a therapeutically effective amount of a compound of formula (I) or formula (II).

Another embodiment of the present invention relates to a method for treating a patient suffering from a disease or disorder ameliorated by inhibition of casein kinase Iε activity comprising administering to said patient a therapeutically effective amount of a compound of formula I or formula II.

A further embodiment of the present invention relates to a process for preparing a compound of formula (I) or formula (II).

DETAILED DESCRIPTION OF THE INVENTION

As used herein, "stereoisomer" is a general term used for all isomers of individual molecules that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers). The compounds of the present invention may have asymmetric centers and occur as racemates, racemic mixtures, individual diastereoisomers, or enantiomers, or may exist as geometric isomers, with all isomeric forms of said compounds being included in the present invention.

As used herein, "R" and "S" are used as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counter-clockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon at the chiral center and "L", that of the isomer in which it is on the left.

As used herein, "tautomer" or "tautomerism" refers to the coexistence of two (or more) compounds that differ from each other only in the position of one (or more) mobile atoms and in electron distribution, for example, keto-enol tautomers or tautomerism.

As used herein, "alkyl" refers to a saturated linear or branched chain aliphatic hydrocarbon group having from one to six carbon atoms, and includes methyl, ethyl, propyl, isopropyl, butyl, sec-butyl, tert-butyl and the like groups. Included within the meaning of "alkyl" are "alkylene" or "alkylenyl" as are defined herein below.

As used herein "alkylene" or "alkylenyl" refers to a linear or branched, divalent, saturated aliphatic chain of one to six carbons and includes methylenyl, ethylenyl, propylenyl, isopropylenyl, butylenyl, isobutylenyl, t-butylenyl, pentylenyl, isopentylenyl, hexylenyl and the like groups.

As used herein "alkenyl" refers to a linear or branched monovalent unsaturated aliphatic chain having from two to six carbon atoms and includes ethenyl (also known as vinyl), 1-methylethenyl, 1-methyl-1-propenyl, 1-butenyl, 1-hexenyl, 2-methyl-2-propenyl, 2,4-hexadienyl, 1-propenyl, 2-propenyl, 2-butenyl, 2-pentenyl, and the like groups.

As used herein "alkynyl" is a linear or branched monovalent unsaturated aliphatic having from two to six carbon atoms with at least one triple bond and includes ethynyl, 1-propynyl, 1-butynyl, 1-hexynyl, 2-propynyl, 2-butynyl, 2-pentynyl and the like groups.

As used herein, "alkoxy" or "alkyloxy" refers to a monovalent substituent which consists of a linear or branched alkyl chain having from one to six carbon atoms linked through an ether oxygen atom and having its free valence bond from the ether oxygen, and includes methoxy, ethoxy, propoxy, isopropoxy, butoxy, sec-butoxy, tert-butoxy and the like groups.

As used herein, "alkylthio" refers to a monovalent substituent which consists of a linear or branched alkyl chain having from one to six carbon atoms linked through a sulfur atom and having its free valence bond from the sulfur, and includes methylthio, ethylthio, propylthio, isopropylthio, butylthio, sec-butylthio, tert-butylthio and the like groups.

As used herein "alkenyloxy" refers to a linear or branched monovalent unsaturated aliphatic chain having from two to six carbon atoms linked through an ether oxygen atom and having its free valence bond from the ether oxygen, and includes ethenyloxy (also known as vinyloxy), 1-methylethenyloxy, 1-methyl-1-propenyloxy, 1-butenyloxy, 1-hexenyloxy, 2-methyl-2-propenyl, 2,4-hexadienyloxy, 1-propenyloxy, 2-propenyloxy, 2-butenyloxy, 2-pentenyloxy, and the like groups.

As used herein "alkynyloxy" refers to a linear or branched monovalent unsaturated aliphatic chain having from two to six carbon atoms with at least one triple bond linked through an ether oxygen atom and having its free valence bond from the ether oxygen, and includes ethynyloxy, 1-propynyloxy, 1-butynyloxy, 1-hexynyloxy, 2-propynyloxy, 2-butynyloxy, 2-pentynyloxy and the like groups.

As used herein the term $C_3$-$C_8$cycloalkyl refers to a saturated hydrocarbon ring structure containing from three to eight carbon atoms and includes cyclopropyl, cyclobutyl, cyclopentyl, cyclohexyl, cycloheptyl, and the like.

As used herein, "aryl" or "Ar" means any stable monocyclic, bicyclic or tricyclic carbon ring of up to seven members in each ring, wherein at least one ring is aromatic and unsubstituted or substituted with from one to three substituents selected from the group consisting of methylenedioxy, hydroxy, $C_1$-$C_6$alkoxy, halogen, $C_1$-$C_6$alkyl, $C_2$-$C_6$alkenyl, $C_2$-$C_6$alkynyl, trifluoromethyl, trifluoromethoxy, —$NO_2$, —$NH_2$, —NH($C_1$-$C_6$alkyl), —N($C_1$-$C_6$alkyl)$_2$, —NH-acyl, and —N($C_1$-$C_6$alkyl)acyl. Examples of "aryl" or "Ar" include phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-trifluoromethylphenyl, 3-trifluoromethylphenyl, 4-trifluoromethylphenyl, 2-methoxyphenyl, 3-methoxyphenyl, 4-methoxyphenyl, 2-aminophenyl, 3-aminophenyl, 4-aminophenyl, 2-methylphenyl, 3-methylphenyl, 4-methylphenyl, 2-nitrophenyl, 3-nitrophenyl, 4-nitrophenyl, 2,4-dichlorophenyl, 2,3-dichlorophenyl, 3,5-dimethylphenyl, 2-trifluoromethoxyphenyl, 3-trifluoromethoxyphenyl, 4-trifluoromethoxyphenyl, naphthyl, tetrahydronaphthyl and biphenyl.

As used herein, the term "aryl-($C_1$-$C_6$alkyl)" refers to an aryl group as defined above linked by a linear or branched alkylene chain containing one to six carbon atoms and having its free valence bond from one of the alkylene chain carbons. Examples of "aryl-($C_1$-$C_6$alkyl)" include phenylmethyl (benzyl), phenylethyl, p-methoxybenzyl, p-fluorobenzyl, p-chlorobenzyl and the like groups.

As used herein, the term "aryl-($C_1$-$C_6$alkoxy)" refers to an aryl group as defined above linked by a linear or branched alkylene chain containing one to six carbon atoms linked through an ether oxygen atom and having its free valence bond from the ether oxygen. Examples of aryl-($C_1$-$C_6$alkoxy) include phenylmethoxy (benzyloxy), phenylethoxy, and the like groups.

As used herein, the term "aryl-($C_1$-$C_6$alkylamino)" refers to an aryl group as defined above linked by a linear or branched alkylene chain containing one to six carbon atoms linked through a nitrogen atom and having its free valence bond from the nitrogen wherein said nitrogen is optionally substituted by a hydrogen or a $C_1$-$C_6$alkyl. Examples of aryl-($C_1$-$C_6$alkylamino) include phenylmethylamino (benzylamino), phenylethylamino, N-methyl-N-benzylamino and the like groups.

As used herein, the term "aryl-($C_1$-$C_6$alkylthio)" refers to an aryl group as defined above linked by a linear or branched alkylene chain containing one to six carbon atoms linked through a sulfur atom and having its free valence bond from the sulfur. Examples of aryl-($C_1$-$C_6$alkylthio) include phenylmethylthio (benzylthio), phenylethylthio, and the like groups.

As used herein, the term "acyl" refers to a H—(C=O)—, $C_1$-$C_6$alkyl-(C=O)—, aryl-(C=O)—, aryl($C_1$-$C_6$alkyl)-(C=O)—, heterocycle-(C=O)—, or heterocycle($C_1$-$C_6$alkyl)-(C=O)— group, wherein alkyl, aryl and heterocycle are as defined herein, and having its free valence bond from the carbonyl (C=O) moiety. Included within the meaning of acyl are acetyl, propionyl, butyryl, isobutyryl, trifluoroacetyl, trichloroacetyl, benzoyl and the like groups.

As used herein, "heterocycle" or "heterocyclic" means a stable 5- to 7-membered monocyclic or stable 8- to 11-membered bicyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. The heterocyclic ring may be unsubstituted or substituted with from one to three substituents selected from the group consisting of $C_1$-$C_6$alkoxy, hydroxy, halogen, $C_1$-$C_6$alkyl, $C_2$-$C_6$alkenyl, $C_2$-$C_6$alkynyl, trifluoromethyl, trifluoromethoxy, —$NO_2$, —$NH_2$, —NH($C_1$-$C_6$alkyl), —N($C_1$-$C_6$alkyl)$_2$, —NH-acyl, and —N($C_1$-$C_6$alkyl)acyl. Examples of such heterocyclic elements include piperidinyl, piperazinyl, 2-oxopiperazinyl, 2-oxopiperidinyl, 2-oxopyrrolidinyl, 2-oxoazepinyl, azepinyl, pyrrolyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoxazolyl, furyl, tetrahydrofuryl, benzofuranyl, tetrahydropyranyl, thienyl, benzothienyl, thiomorpholinyl, and oxadiazolyl.

As used herein, the term "heterocycle-($C_1$-$C_6$alkyl)" or "heterocyclic-($C_1$-$C_6$alkyl)" refers to a heterocycle or heterocyclic ring as defined above linked by a linear or branched alkylene chain containing one to six carbon atoms to another carbon atom or to a heteroatom selected from the group consisting of O, N and S. Included within the meaning of heterocycle($C_1$-$C_6$alkyl) or heterocyclic($C_1$-$C_6$alkyl) are 4-pyridinylmethyl, 3-pyridinylmethyl, 2-pyridinylmethyl, 2-furanmethyl, 2-thenyl (2-thiophenemethyl), 5-nitro-2-thenyl, 5-(2-chlorophenyl)-2-furanmethyl, 1-(phenylsulfonyl)-1H-pyrrole-2-methyl and the like groups.

As used herein, the term "heterocycle-($C_1$-$C_6$alkoxy)" or "heterocyclic-($C_1$-$C_6$alkoxy)" refers to a heterocycle or heterocyclic ring as defined above linked by a linear or branched alkylene chain containing one to six carbon atoms linked through an ether oxygen atom and having its free valence bond from the ether oxygen. Included within the meaning of heterocycle($C_1$-$C_6$alkoxy) or heterocyclic($C_1$-$C_6$alkoxy) are 2-thienylmethoxy, 3-thienylmethoxy, 2-furanmethoxy, 3-furanmethoxy, 4-pyridinylmethoxy, 3-pyridinylmethoxy, 2-pyridinylmethoxy and the like groups.

As used herein, the term "heterocycle-($C_1$-$C_6$alkylamino)" or "heterocyclic-($C_1$-$C_6$alkylamino)" refers to a heterocycle or heterocyclic ring as defined above linked by a linear or branched alkylene chain containing one to six carbon atoms linked through a nitrogen atom and having its free valence bond from the nitrogen wherein said nitrogen is optionally substituted by a hydrogen or a $C_1$-$C_6$alkyl. Included within the meaning of heterocycle($C_1$-$C_6$alkylamino) or heterocyclic($C_1$-$C_6$alkylamino) are 2-thienylmethylamino, 3-thienylmethylamino, 2-furanmethylamino, 3-furanmethylamino, 4-pyridinylmethylamino, 3-pyridinylmethylamino, 2-pyridinylmethylamino and the like groups.

As used herein, the term "heterocycle-($C_1$-$C_6$alkylthio)" or "heterocyclic-($C_1$-$C_6$alkylthio)" refers to a heterocycle or heterocyclic ring as defined above linked by a linear or branched alkylene chain containing one to six carbon atoms linked through a sulfur atom and having its free valence bond from the sulfur. Included within the meaning of heterocycle ($C_1$-$C_6$alkylthio) or heterocyclic($C_1$-$C_6$alkylthio) are 2-thienylmethylthio, 3-thienylmethylthio, 2-furanmethylthio, 3-furanmethylthio, 4-pyridinylmethylthio, 3-pyridinylmethylthio, 2-pyridinylmethylthio and the like groups.

As used herein, "halogen", "hal" or "halo" refers to a member of the family of fluorine, chlorine, bromine or iodine.

When any variable (e.g., aryl, heterocycle, $R_1$, $R_2$, $R_3$, $R_4$, $R_5$, $R_6$, $R_7$, $R_8$, X) occurs more than one time in any constituent or in a compound of formula (I) or formula (II) of this invention, its definition on each occurrence is independent of its definition at every other occurrence unless indicated otherwise. Also, combinations of substituents and/or variables are permissible only if such combinations result in stable compounds.

As used herein, "treat", "treating" or "treatment" refers to:
(i) preventing a disease, disorder or condition from occurring in a patient that may be predisposed to the disease, disorder and/or condition, but has not yet been diagnosed as having it;
(ii) inhibiting a disease, disorder or condition, i.e., arresting its development; or
(iii) relieving a disease, disorder or condition, i.e., causing regression of the disease, disorder and/or condition.

As used herein, the term "patient" refers to a warm blooded animal such as a mammal which is afflicted with a particular disease, disorder or condition. It is explicitly understood that guinea pigs, dogs, cats, rats, mice, horses, cattle, sheep, and humans are examples of animals within the scope of the meaning of the term.

As used herein, "disease" refers to an illness, sickness or an interruption, cessation or disorder of body functions, systems or organs.

As used herein, "disorder" refers to a disturbance of function, structure or both resulting from a genetic or embryologic failure in development, or from exogenous factors such as poison, injury or disease.

As used herein, "condition" refers to a state of being, health or physical fitness.

As used herein, "prophylaxis" refers to the prevention of disease.

As used herein, the term "sleep disorder", "sleep disorders" or "sleep disturbance" means insomnia.

As used herein, the term "insomnia" means the inability to sleep in the absence of external impediments, such as noise, bright light, etc., during the period when sleep should normally occur and the inability to sleep may vary in degree from restlessness or disturbed slumber to a curtailment of the normal length of sleep or to absolute wakefulness. The term "insomnia" includes primary insomnia, insomnia related to a mental disorder, substance-induced insomnia and circadian rhythm insomnia that is insomnia due to a change in the normal sleep-wake schedule (shift changes, shift work sleep disorder, jet lag or jet lag syndrome, etc.).

As used herein the term "primary insomnia" means difficulty in initiating sleep, in maintaining sleep or having restorative sleep which is not caused by a mental disorder or due to physiological effects of taking or withdrawing from certain substances (substance-induced insomnia).

As used herein the term "circadian rhythm sleep disorder" includes jet lag or jet lag syndrome, shift work sleep disorder, advanced sleep phase syndrome and delayed sleep phase syndrome.

As used herein the term "effective inhibitory amount of a compound" or "effective casein kinase Iε inhibitory amount of a compound" means enough of a compound that becomes bioavailable through the appropriate route of administration to treat a patient afflicted with a disease, disorder or condition amenable to such treatment.

As used herein the term "a therapeutically effective amount" means an amount of a compound which is effective in treating the named disease, disorder or condition.

As used herein, the phrase "lengthening of circadian rhythm period" refers to increasing the interval between seminal events in a process that occurs regularly with a frequency of approximately once every 24 hours.

As used herein, the phrase "shortening of circadian rhythm period" refers to decreasing the interval between seminal events in a process that occurs regularly with a frequency of approximately once every 24 hours.

As used herein, the term "pharmaceutically acceptable salt" is intended to apply to any salt, whether previously known or future discovered, that is used by one skilled in the art that is a non-toxic organic or inorganic addition salt which is suitable for use as a pharmaceutical. Illustrative bases which form suitable salts include alkali metal or alkaline-earth metal hydroxides such as sodium, potassium, calcium or magnesium hydroxides; ammonia and aliphatic, cyclic or aromatic amines such as methylamine, dimethylamine, triethylamine, diethylamine, isopropyldiethylamine, pyridine and picoline. Illustrative acids which form suitable salts include inorganic acids such as, for example, hydrochloric, hydrobromic, sulfuric, phosphoric and like acids, and organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids, and organic sulfonic acids such as methanesulfonic, benzenesulfonic and p-toluenesulfonic acids.

As used herein, "pharmaceutical carrier" or "pharmaceutically acceptable carrier" refers to known pharmaceutical excipients useful in formulating pharmaceutically active compounds for administration, and which are substantially nontoxic and non-sensitizing under conditions of use. The exact proportion of these excipients is determined by the solubility and chemical properties of the active compound, the chosen route of administration as well as standard pharmaceutical practice. In practicing the methods of this invention, the active ingredient is preferably incorporated into a composition containing a pharmaceutical carrier, although the compounds are effective and can be administered, in and of themselves. That said, the proportion of active ingredient can vary from about 1% to about 90% by weight.

Further abbreviations that may appear in this application shall have the following meanings:

Me (methyl), Et (ethyl), Ph (phenyl), Et$_3$N (triethylamine), p-TsOH (para-toluene sulfonic acid), TsCl (para-toluenesulfonyl chloride), hept (heptane), DMF (dimethylformamide), NMP (1-methyl-2-pyrrolidinone or N-methyl-2-pyrrolidinone), IPA (isopropanol or isopropyl alcohol), DBU (1,8-diazabicyclo[5.4.0]undec-7-ene), DBN (1,5-diazabicyclo[4.3.0]non-5-ene), rt or r.t. (room temperature or ambient temperature), min or min. (minutes), h (hour or hours), UV (ultraviolet), LCMS (liquid chromatography mass spectrometry), t-Boc or Boc (tert-butoxycarbonyl), Bn (benzyl), t-Bu (tertiary butyl), i-Pr (isopropyl), TFA (trifluoroacetic acid), HOAc (acetic acid), EtOAc (ethyl acetate), Et$_2$O (diethylether), EtOH (ethanol), DIEA (diisopropylethylamine), EDC (1-(3-dimethylaminopropyl)-3-ethylcarbodiimide hydrochloride); HOBT (1-hydroxybenzotriazole), g (gram), mg (milligram), μg (microgram), ng (nanogram), mL (milliliter), μL (microliter), L (liter), HPLC (high-performance liquid chromatography), TLC, tlc or Tlc (thin layer chromatography), g/L (grams per liter), SiO$_2$ (silica gel), L/min (liters per minute), mL/min (milliliters per minute), mmol (millimole), M (molar), mM (millimolar), μM (micromolar), nM (nanomolar), μCi (microCurie), CPM (counts per minute), rpm (revolutions per minute), mm (millimeter), μm (micrometer), μ (micron), nm (nanometer), ppm (parts per million), psi (pounds per square inch), eq. or equiv. (equivalent), R$_T$ (retention time), ° C. (degrees Celsius), and K (Kelvin).

Accordingly, a broad embodiment of the invention is directed to a compound of formula (I) or formula (II):

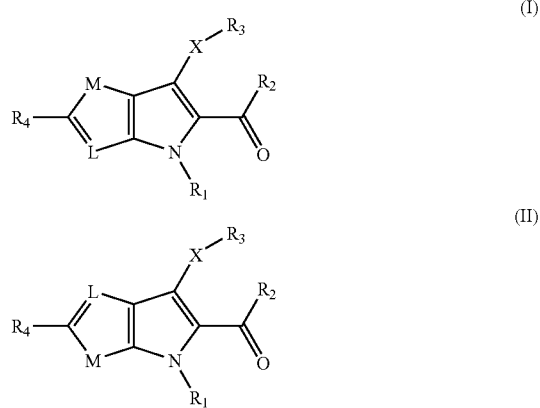

wherein X is S or S(O)$_n$; R$_1$ is H or C$_1$-C$_6$alkyl; R$_2$ is NR$_5$R$_6$; R$_3$ is aryl or heterocycle; R$_4$ is H, C$_1$-C$_6$alkyl, C$_2$-C$_6$alkenyl, C$_2$-C$_6$alkynyl, aryl-(C$_1$-C$_6$alkyl), heterocycle-(C$_1$-C$_6$alkyl), C$_1$-C$_6$alkoxy, aryl-(C$_1$-C$_6$alkoxy), heterocycle-(C$_1$-C$_6$alkoxy), CF$_3$, halogen, SH, C$_1$-C$_6$alkylthio, aryl-(C$_1$-C$_6$alkylthio), heterocycle-(C$_1$-C$_6$alkylthio), NO$_2$, NH$_2$, NR$_5$R$_6$, aryl-(C$_1$-C$_6$alkylamino), heterocycle-(C$_1$-C$_6$alkylamino), or XR$_3$ wherein X and R$_3$ are as defined above; R$_5$ is H or C$_1$-C$_6$alkyl; R$_6$ is H or C$_1$-C$_6$alkyl; L is N or CR$_7$ wherein R$_7$ is H or C$_1$-C$_6$alkyl; M is S, O or NR$_8$ wherein R$_8$ is H, C$_1$-C$_6$alkyl, aryl-(C$_1$-C$_6$alkyl), heterocycle-(C$_1$-C$_6$alkyl) or acyl; and n is 1 or 2.

A further embodiment of this invention relates to compounds of formula (I) or formula (II) wherein M and X are each S.

Another embodiment of this invention relates to compounds of formula (I) wherein L is CR$_7$ and M and X are each S.

A further embodiment of this invention relates to compounds wherein of formula (I) wherein M and X are each S, L is CR$_7$, and R$_7$ is H. The following compounds are representative examples within the scope of this embodiment:
6-phenylsulfanyl-4H-thieno[3,2-b]pyrrole-5-carboxylic acid amide,
6-(3-fluorophenyl-sulfanyl)-4H-thieno[3,2-b]pyrrole-5-carboxylic acid amide,
6-(4-chlorophenyl-sulfanyl)-4H-thieno[3,2-b]pyrrole-5-carboxylic acid amide,
6-(2-aminophenyl-sulfanyl)-4H-thieno[3,2-b]pyrrole-5-carboxylic acid amide,
6-(pyridin-2-ylsulfanyl)-4H-thieno[3,2-b]pyrrole-5-carboxylic acid amide,
6-p-tolylsulfanyl-4H-thieno[3,2-b]pyrrole-5-carboxylic acid amide,
6-(thiophen-2-yl-sulfanyl)-4H-thieno[3,2-b]pyrrole-5-carboxylic acid amide,
6-(3,5-dichloro-phenylsulfanyl)-4H-thieno[3,2-b]pyrrole-5-carboxylic acid amide,
6-(pyridin-4-ylsulfanyl)-4H-thieno[3,2-b]pyrrole-5-carboxylic acid amide,
6-m-tolylsulfanyl-4H-thieno[3,2-b]pyrrole-5-carboxylic acid amide,
6-o-tolylsulfanyl-4H-thieno[3,2-b]pyrrole-5-carboxylic acid amide,
6-(2,3-dichloro-phenylsulfanyl)-4H-thieno[3,2-b]pyrrole-5-carboxylic acid amide,
6-(2,5-dichloro-phenylsulfanyl)-4H-thieno[3,2-b]pyrrole-5-carboxylic acid amide,
6-(2-ethyl-phenylsulfanyl)-4H-thieno[3,2-b]pyrrole-5-carboxylic acid amide,
6-(3-bromo-phenylsulfanyl)-4H-thieno[3,2-b]pyrrole-5-carboxylic acid amide,
6-(3,5-dimethyl-phenylsulfanyl)-4H-thieno[3,2-b]pyrrole-5-carboxylic acid amide,
6-(3-methoxy-phenylsulfanyl)-4H-thieno[3,2-b]pyrrole-5-carboxylic acid amide,
6-(2-methoxy-phenylsulfanyl)-4H-thieno[3,2-b]pyrrole-5-carboxylic acid amide,
6-(2-trifluoromethyl-phenylsulfanyl)-4H-thieno[3,2-b]pyrrole-5-carboxylic acid amide,
6-(2-fluoro-phenylsulfanyl)-4H-thieno[3,2-b]pyrrole-5-carboxylic acid amide, and
6-(3-trifluoromethoxy-phenylsulfanyl)-4H-thieno[3,2-b]pyrrole-5-carboxylic acid amide.

Another embodiment of this invention relates to compounds of formula (I) wherein L is N and M and X are each S. The following compounds are representative examples within the scope of this embodiment:
6-phenylsulfanyl-4H-pyrrolo[2,3-d]thiazole-5-carboxylic acid amide,
6-(3-fluoro-phenylsulfanyl)-4H-pyrrolo[2,3-d]thiazole-5-carboxylic acid amide, and
6-(pyridin-2-ylsulfanyl)-4H-pyrrolo[2,3-d]thiazole-5-carboxylic acid amide.

Another embodiment of this invention relates to compounds of formula (II) wherein L is CR$_7$ and M and X are each S.

A further embodiment of this invention relates to compounds wherein of formula (II) wherein M and X are each S, L is CR₇, and R₇ is H. The following compounds are representative examples within the scope of this embodiment:
4-(pyridin-2-ylsulfanyl)-6H-thieno[2,3-b]pyrrole-5-carboxylic acid amide,
4-(phenylsulfanyl)-6H-thieno[2,3-b]pyrrole-5-carboxylic acid amide,
6-(3-fluorophenyl-sulfanyl)-6H-thieno[2,3-b]pyrrole-5-carboxylic acid amide,
4-(pyridin-4-ylsulfanyl)-6H-thieno[2,3-b]-pyrrole-5-carboxylic acid amide,
4-(3,5-dichlorophenyl-sulfanyl)-6H-thieno[2,3-b]pyrrole-5-carboxylic acid amide,
4-(thiophen-2-yl-sulfanyl)-6H-thieno[2,3-b]pyrrole-5-carboxylic acid amide,
4-(3-bromophenyl-sulfanyl)-6H-thieno[2,3-b]pyrrole-5-carboxylic acid amide,
4-(3-methoxyphenyl-sulfanyl)-6H-thieno[2,3-b]pyrrole-5-carboxylic acid amide,
4-(2-methoxyphenyl-sulfanyl)-6H-thieno[2,3-b]pyrrole-5-carboxylic acid amide,
4-(3-chlorophenyl-sulfanyl)-6H-thieno[2,3-b]pyrrole-5-carboxylic acid amide, and
4-(3-methylphenyl-sulfanyl)-6H-thieno[2,3-b]pyrrole-5-carboxylic acid amide.

Another embodiment of this invention relates to compounds of formula (II) wherein L is N and M and X are each S. The following compounds are representative examples within the scope of this embodiment:
2-methyl-6-phenyl-sulfanyl-4H-pyrrolo[3,2-d]thiazole-5-carboxylic acid amide,
6-(3-methoxyphenyl-sulfanyl)-2-methyl-4H-pyrrolo[3,2-d]thiazole-5-carboxylic acid amide,
6-(3-fluorophenyl-sulfanyl)-2-methyl-4H-pyrrolo[3,2-d]thiazole-5-carboxylic acid amide,
6-(3-chlorophenyl-sulfanyl)-2-methyl-4H-pyrrolo[3,2-d]thiazole-5-carboxylic acid amide,
6-(3-trifluoromethoxy-phenylsulfanyl)-2-methyl-4H-pyrrolo[3,2-d]thiazole-5-carboxylic acid amide,
2,6-bis-phenylsulfanyl-4H-pyrrolo[3,2-d]thiazole-5-carboxylic acid amide,
2,6-bis-(3-methoxy-phenylsulfanyl)-4H-pyrrolo[3,2-d]thiazole-5-carboxylic acid amide,
6-phenylsulfanyl-4H-pyrrolo[3,2-d]thiazole-5-carboxylic acid amide, and
6-(3-methoxyphenyl-sulfanyl)-4H-pyrrolo[3,2-d]thiazole-5-carboxylic acid amide.

Another embodiment of the present invention relates to a method for inhibiting casein kinase Iε activity in a patient that comprises administering to said patient a therapeutically effective amount of a compound of formula (I) or formula (II) that results in a lengthening of circadian rhythm period.

Another embodiment of the present invention relates to a method for treating a patient suffering from a disease or disorder ameliorated by inhibition of casein kinase Iε activity that comprises administering to said patient a therapeutically effective amount of a compound of formula (I) or formula (II) wherein said inhibition of casein kinase Iε activity results in a lengthening of circadian rhythm period.

The compounds of the present invention can be prepared by processes analogous to those known in the art. Reaction schemes 1, 2 and 3, and the corresponding descriptive text, describe the preparation of the various compounds of the invention. The disclosed methods and examples are provided for illustration purposes and in no way limit the scope of the present invention. Alternative reagents, reaction conditions, and other combinations and permutations of the steps herein described to arrive at individual compounds are readily apparent to one of ordinary skill in the art. Tables 1, 2, 3 and 4 provide summaries of the example compounds, and biological data for example compounds of the invention is summarized in Table 5.

Chemical Synthesis

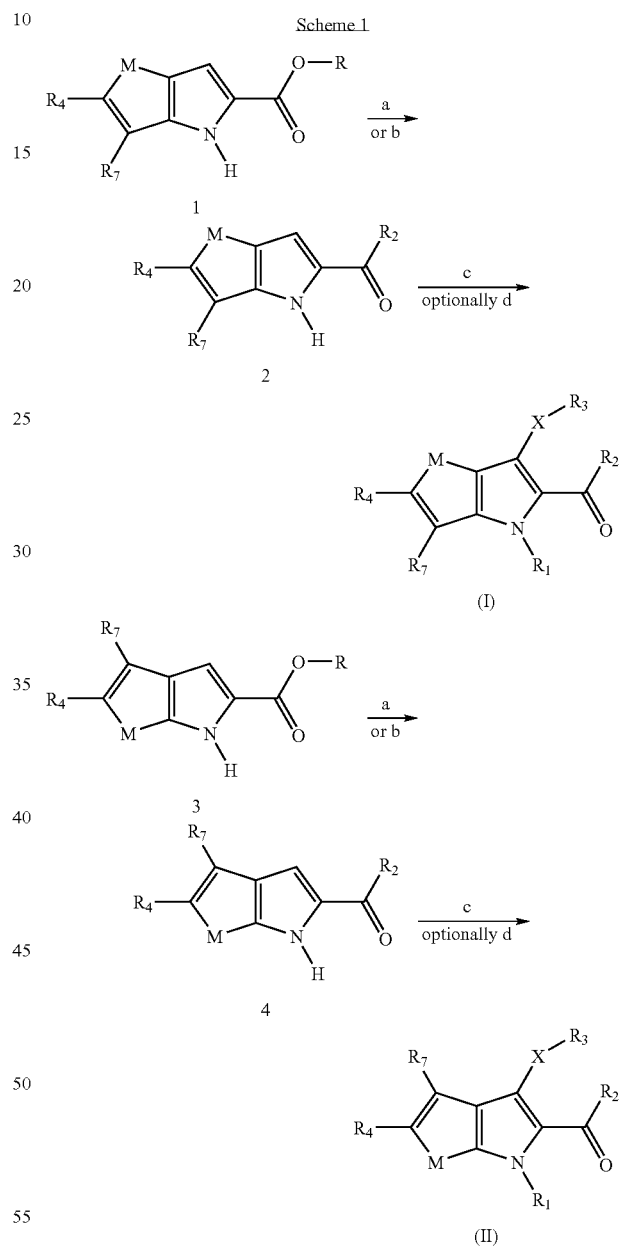

Scheme 1 describes the synthesis of 4H-thieno[3,2-b]pyrroles (M is S), 4H-furo[3,2-b]pyrroles (M is O), and 1,4-dihydropyrrolo[3,2-b]pyrroles (M is NR₈) of formula (I) wherein L is CR₇, and the synthesis of 6H-thieno[2,3-b]pyrroles (M is S), 6H-furo[2,3-b]pyrroles (M is O), and 1,6-dihydropyrrolo[2,3-b]pyrroles (M is NR₈) of formula (II) wherein L is CR₇ from known or commercially available esters or carboxylic acids 1 and 3, respectively, wherein R is alkyl or H.

In scheme 1, step a, starting esters 1 or 3, wherein R is alkyl, are converted to amides 2 or 4, respectively, by methods well known to one skilled in the art. Thus, treating a mixture of about 7M ammonia and ester 1 or 3 in a suitable polar solvent, such as for example methanol or ethanol, with a chip of lithium hydroxide and heating the resultant mixture in a pressure vessel at about 100° C. for about 16 hours provides, after chromatographic purification as is well known to one skilled in the art, primary amide 2 or 4, respectively. Alternatively, other reaction conditions well known to one skilled in the art may be employed, such as treating a solution of ester 1 or 3 in a suitable polar solvent, such as for example methanol or ethanol, with about 5M to about 7M ammonia solution for about one day to about three days at ambient temperature, or by heating the solution to about 55° C. for about 10 hours, provides primary amide 2 or 4, respectively, after isolation by methods well known to one skilled in the art. Alternatively, ester 1 or 3 may be suspended in a mixture of concentrated ammonium hydroxide solution and lithium chloride at ambient temperature for about three to about five days until thin layer chromatographic analysis, or other suitable chromatographic analysis as is well known to one skilled in the art, indicates that the reaction is substantially complete. Primary amides 2 or 4 are isolated from the reaction mixture by methods well known to one skilled in the art. If primary or secondary $C_1$-$C_6$alkylamines are employed in place of ammonia or ammonium hydroxide, there is obtained the corresponding secondary and tertiary amides 2 or 4 wherein $R_2$ is $NR_5R_6$, $R_5$ is H or $C_1$-$C_6$alkyl and $R_6$ is $C_1$-$C_6$alkyl.

As shown in scheme 1, step b, commercially available or known carboxylic acids 1 or 3 (wherein R is H) may be converted to amides 2 or 4, respectively, by methods well known to one skilled in the art. Where desired, carboxylic acids 1 or 3 (R is H) may also be prepared by hydrolysis of the corresponding esters 1 or 3 (R is alkyl) by methods well known to one skilled in the art. For example, a suitable base, such as for example potassium hydroxide, sodium hydroxide, lithium hydroxide and like bases, is added to a mixture of ester 1 or 3 in a suitable solvent such as for example a mixture of tetrahydrofuran and water. The mixture is heated at about 90° C. to about 110° C. for about 0.5 hour to about 2 hours. The product is recovered as a salt by filtration and the filtrate is concentrated to provide additional material as a residue. The filter cake and residue are combined and acidified by methods well known to one skilled in the art, such as for example acidification with a suitable acid such as acetic acid in a suitable solvent such as methanol, ethanol and like solvents, to provide carboxylic acids 1 or 3, respectively, wherein R is H. As shown in scheme I, step b, for example, a solution of carboxylic acid 1 or 3 in a suitable solvent such as dimethylformamide is treated with a base such as diisopropylethylamine, a carbodiimide such as for example (1-(3-dimethylamino-propyl)-3-ethylcarbodiimide hydrochloride, 1-hydroxybenzotriazole and ammonium chloride. When the reaction is complete as determined by thin layer chromatography, or other suitable chromatographic analysis as is well known to one skilled in the art, the mixture is diluted with a suitable solvent, and the product is isolated and chromatographically purified by methods well known to one skilled in the art to provide primary amides 2 or 4, respectively, wherein $R_2$ is $NH_2$. If primary or secondary $C_1$-$C_6$alkylamines are employed in place of ammonium chloride, there is obtained the corresponding secondary and tertiary amides 2 or 4 wherein $R_2$ is $NR_5R_6$, $R_5$ is H or $C_1$-$C_6$alkyl and $R_6$ is $C_1$-$C_6$alkyl.

As shown in scheme 1, step c, intermediate amides 2 or 4 are each thioarylated at the 3-position of the amide-bearing pyrrole ring by methods well known to one skilled in the art. For example, a suspension of intermediate amide 2 or 4 in a suitable solvent, such as for example dimethylformamide or NMP, is treated with a suitable base, such as for example sodium hydride or lithium hydride, at ambient temperature, followed by treatment with a suitable diaryldisulfide or diheterocycledisulfide, and then the mixture is stirred at ambient temperature to about 100° C. for about 12 hours to about 20 hours. The course of the reaction is followed by thin layer chromatographic analysis or other chromatographic methods as are well known to one skilled in the art. When complete, the reaction is worked-up by extractive methods as are well known to one skilled in the art. The desired 4H-thieno[3,2-b] pyrroles (M is S), 4H-furo[3,2-b]pyrroles (M is O), and 1,4-dihydropyrrolo[3,2-b]pyrroles (M is $NR_8$) of formula (I), wherein L is $CR_7$, X is S and $R_3$ is aryl or heterocycle, and 6H-thieno[2,3-b]pyrroles (M is S), 6H-furo[2,3-b]pyrroles (M is O), and 1,6-dihydropyrrolo[2,3-b]pyrroles (M is $NR_8$) of formula (II), wherein L is $CR_7$, X is S and $R_3$ is aryl or heterocycle, are each isolated and chromatographically purified by methods as are well known to one skilled in the art.

Alternatively, a mixture of the diaryldisulfide or diheterocycledisulfide and about one equivalent of cesium carbonate in a suitable solvent, such as for example dimethylformamide or NMP, is treated with intermediate amide 2 or 4, and then the mixture is heated at about 80° C. to about 120° C. for about one to about six hours. The reaction is monitored by thin layer chromatography or other chromatographic methods as are well known to one skilled in the art. The desired 4H-thieno[3,2-b]pyrroles (M is S), 4H-furo[3,2-b]pyrroles (M is O) and 1,4-dihydropyrrolo[3,2-b]pyrroles (M is $NR_8$) of formula (I), wherein L is $CR_7$, X is S and $R_3$ is aryl or heterocycle, and 6H-thieno[2,3-b]pyrroles (M is S), 6H-furo [2,3-b]pyrroles (M is O) and 1,6-dihydropyrrolo[2,3-b]pyrroles (M is $NR_8$) of formula (II), wherein L is $CR_7$, X is S and $R_3$ is aryl or heterocycle, are each isolated and chromatographically purified by methods well known to one skilled in the art.

As shown in scheme 1, optional step d, the nitrogen of the pyrrole ring of a compound of formula (I) or formula (II), wherein $R_1$ is H, is N-alkylated by treating a solution of the compound formula (I) or formula (II) wherein $R_1$ is H and a suitable solvent, such as for example 1,3-dimethyl-3,4,5,6-tetrahydro-2(1H)-pyrimidinone with a $C_1$-$C_6$-dialkylsulfate and a suitable base, such as for example cesium carbonate, at ambient temperature for about 12 hours to about 20 hours. Completion of the reaction is determined by thin layer chromatographic analysis or other chromatographic methods as are well known to one skilled in the art. When complete, the reaction mixture is diluted with water and the compound of formula (I) or formula (II) wherein $R_1$ is $C_1$-$C_6$alkyl is isolated and purified by methods well known to one skilled in the art.

Alternatively, the nitrogen of the pyrrole ring of a scheme 1 compound of formula (I) or formula (II) is alkylated by treating a pyridine solution of a compound of formula (I) or formula (II), wherein $R_1$ is H, with a $C_1$-$C_6$-alkyl halide in the presence of a suitable base such as for example cesium carbonate with heating for about 0.25 hour to about 3 hours. The reaction mixture is cooled, diluted with water or concentrated to dryness, and extracted with ethyl acetate. Concentration and subsequent purification by chromatographic methods as are well known to one skilled in the art provides the scheme 1 compound of formula (I) or formula (II) wherein $R_1$ is $C_1$-$C_6$-alkyl.

Additionally, N-alkylation of the pyrrole ring nitrogen of a compound formula (I) or formula (II) wherein $R_1$ is H is achieved by other methods that are well known to one skilled in the art, for example by treatment of a compound formula (I) or formula (II) wherein $R_1$ is H in a suitable polar solvent such as for example dimethylformamide or NMP, with a suitable base, such as for example sodium hydride or potassium t-butoxide, and then a $C_1$-$C_6$alkyl halide such as for example, propyl iodide is added. Completion of the reaction is determined by thin layer chromatographic analysis or other chromatographic methods well known to one skilled in the art. When complete, the reaction mixture is diluted with water and the scheme I compound of formula (I) or formula (II) wherein $R_1$ is $C_1$-$C_6$alkyl is isolated and purified by methods well known to one skilled in the art.

As is well recognized by one skilled in the art, when M is $NR_8$ and $R_8$ is H, under the above described conditions N-alkylation may also occur on the aforesaid $NR_8$ nitrogen to provide scheme 1 compounds of formula (I) or formula (II) wherein $R_1$ and $R_8$ are each the same $C_1$-$C_6$alkyl group. The preparation of starting esters 1 wherein R is ethyl, $R_4$ and $R_7$ is each H, M is $NR_8$ and $R_8$ is methyl is known by thermolysis of 2-azidoacrylates (also known as 2-azidopropenoic acid esters) as is also described in scheme 2 below (H. Hemetsberger and D. Knittel, Monatsh. Chem. (1972) 103(1), 194-204). Starting ester 1 wherein M is $NR_8$ and $R_8$ is $C_1$-$C_6$alkyl is prepared as described and then converted as described in scheme 1 to a compound of formula (I) wherein M is $NR_8$, $R_8$ is $C_1$-$C_6$alkyl and $R_1$ is H or $C_1$-$C_6$alkyl and wherein said $R_1$ and $R_8$ $C_1$-$C_6$alkyl groups may be the same or different. This methodology is also employed to provide similarly substituted esters 3 that are converted as described in scheme 1 to a compound of formula (II) wherein $R_8$ is $C_1$-$C_6$alkyl and $R_1$ is H or $C_1$-$C_6$alkyl and wherein said $R_1$ and $R_8$ $C_1$-$C_6$alkyl groups may be the same or different.

Additionally a compound of formula (I) or formula (II) of scheme 1 wherein $R_1$ is H or $C_1$-$C_6$alkyl and X is S, is optionally oxidized to a sulfone or a sulfoxide wherein X is $S(O)_n$, and n is 1 or 2, respectively, by methods well known to one skilled in the art, such as for example, treating a solution of said compound of formula (I) or formula (II) with $H_2O_2$ and $Na_2CO_3$. Alternatively, compound 2 or 4 of scheme 1 is treated with an arylsulfonyl chloride, an arylsulfinyl chloride, a heterocyclesulfonyl chloride or a heterocyclesulfinyl chloride (used in place of the diaryldisulfide or diheterocycledisulfide) as described in step c above, to provide a scheme 1 compound of formula (I) or formula (II) wherein X is $S(O)_n$, n is 1 or 2 and $R_3$ is aryl or heterocycle.

Scheme 2, as shown below, describes the synthesis of 4H-pyrrolo[2,3-d]thiazoles (M is S), 4-H-pyrrolo[2,3-d]oxazoles, (M is O) and 1,4-dihydro-pyrrolo[2,3-d]imidazoles (M is $NR_8$) of formula (I) wherein L is N, and the synthesis of 6H-pyrrolo[3,2-d]thiazoles (M is S), 6H-pyrrolo[3,2-d]oxazoles (M is O), and 3,4-dihydro-pyrrolo[2,3-d]imidazoles (M is $NR_8$) of formula (II) wherein L is N, from known or commercially available starting materials. One skilled in the art readily understands that when L is N, M is $NR_8$ and $R_8$ is H, that the imidazole ring can exist in tautomeric forms. In scheme 2, step a, carboxaldehyde 5 or 7 is condensed with a 2-azidoacetate ester 6 wherein R is alkyl, in the presence of a suitable base such as for example potassium hydroxide, sodium hydroxide or like bases, to provide the corresponding 2-azidopropenoic acid ester 8 or 11, respectively, wherein R is alkyl.

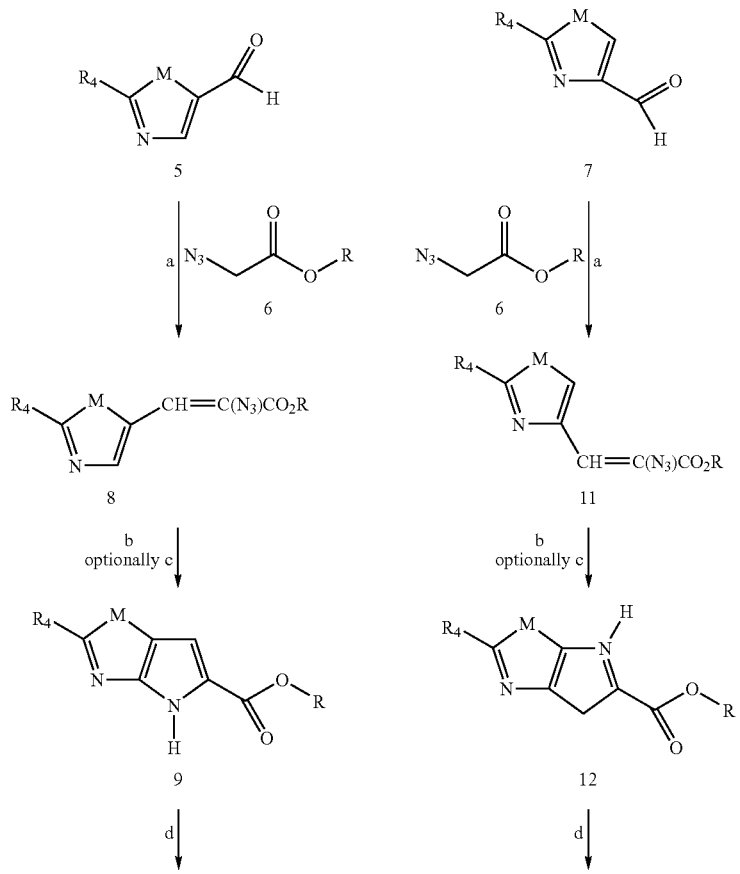

Scheme 2

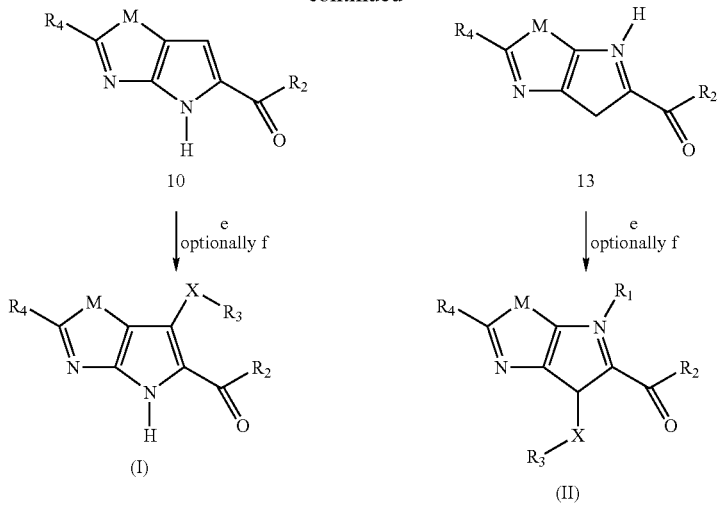

As shown in scheme 2, step b, thermolysis of 2-azidopropenoic acid ester 8 or 11 is effected by heating a mixture of 2-azidopropenoic acid ester 8 or 11 in a suitable solvent such as for example xylene at about 120° C. to about 140° C. for about 30 to 90 minutes to provide, after chromatographic purification by methods well known to one skilled in the art, the corresponding ester 9 or 12, respectively, wherein R is alkyl.

As shown in scheme 2, optional step c, ester 9 or 12 obtained from step b may be hydrolyzed by methods well known to one skilled in the art to provide the corresponding carboxylic acid 9 or 12, respectively, wherein R is H. For example, a suitable base, such as for example potassium hydroxide, sodium hydroxide, lithium hydroxide and like bases, is added to a mixture of ester 9 or 12 and a suitable solvent, such as for example a mixture of tetrahydrofuran and water. The mixture is heated at about 90° C. to about 110° C. for about 0.5 hour to 2 hours. The product is recovered as a salt by filtration and the filtrate is concentrated to provide additional material as a residue. The filter cake and residue are combined and acidified by methods well known to one skilled in the art, such as for example acidification with a suitable acid such as acetic acid in a suitable solvent such as methanol, ethanol and like solvents, to provide carboxylic acid 9 or 12, respectively, wherein R is H.

As shown in scheme 2, step d, ester 9 or 12, wherein R is alkyl, is converted to amide 10 or 13, respectively, as was described above for scheme 1, step a. Alternatively, carboxylic acid 9 or 12, wherein R is H, is converted to the corresponding amide 10 or 13, respectively, by methods as are well known to one skilled in the art and as described in scheme 1, step b. For example, a solution of carboxylic acid 9 or 12 in a suitable solvent such as dimethylformamide is treated with a base such as diisopropylethylamine, a carbodiimide such as for example (1-(3-dimethylamino-propyl)-3-ethylcarbodiimide hydrochloride, 1-hydroxybenzotriazole and ammonium chloride. When the reaction is complete, the mixture is diluted with a suitable solvent, and the product is isolated and chromatographically purified by methods well known to one skilled in the art to afford the corresponding 4H-pyrrolo[2,3-d]thiazole (M is S), 4-H-pyrrolo[2,3-d]oxazole, (M is O) or 1,4-dihydro-pyrrolo[2,3-d]imidazole (M is $NR_8$) primary amide 10, or 6H-pyrrolo[3,2-d]thiazole (M is S), 6H-pyrrolo[3,2-d]oxazole (M is O), or 3,4-dihydro-pyrrolo[2,3-d]imidazole (M is $NR_8$) primary amide 13, respectively, wherein $R_2$ is $NH_2$. If a primary or secondary $C_1$-$C_6$alkylamine is employed in place of ammonium chloride, there is obtained the corresponding secondary or tertiary amide 10 or 13, respectively, wherein $R_2$ is $NR_5R_6$, $R_5$ is H or $C_1$-$C_6$alkyl and $R_6$ is $C_1$-$C_6$alkyl.

As shown in scheme 2, step e, intermediate amide 10 or 13 is thioarylated at the 3-position of the amide bearing pyrrole ring by methods analogous to the methods described above for scheme 1, step c, to provide 4H-pyrrolo[2,3-d]thiazole (M is S), 4-H-pyrrolo[2,3-d]oxazole, (M is O) or 1,4-dihydro-pyrrolo[2,3-d]imidazole (M is $NR_8$) amide of formula (I), or 6H-pyrrolo[3,2-d]thiazole (M is S), 6H-pyrrolo[3,2-d]oxazole (M is O) or 3,4-dihydro-pyrrolo[2,3-d]imidazole (M is $NR_8$) amide of formula (II), respectively, wherein X is S and $R_3$ is aryl or heterocycle.

Wherein $R_4$ is halogen, such as for example Br, in intermediate amide 10 or 13, thioarylation at the 3-position of the amide-bearing pyrrole ring and displacement of the aforesaid halogen atom may both occur under the conditions described. Concomitant displacement of the aforesaid halogen from intermediate amide 10 or 13 under conditions described for step e above employing a diaryldisulfide or diheterocycledisulfide is thus advantageously utilized to provide a scheme 2 compound of formula (I) or formula (II), wherein $R_4$ is an arylthio or a heterocyclethio moiety (that is, $XR_3$) that is identical to the pyrrole ring $XR_3$ moiety wherein X is S and $R_3$ is aryl or heterocycle. Additionally, displacement of the aforesaid halogen atom from intermediate amide 10 or 13, or from an earlier intermediate such as for example an intermediate ester 9 or 12, with an anion prepared by treating an arylthiol or heterocyclethiol with a suitable base also advantageously provides a compound of formula (I) or formula (II) wherein $R_4$ is an arylthio or a heterocyclethio moiety that can be the same or different from the $XR_3$ moiety introduced by thioarylation as described above for scheme 2, step e. Additionally, displacement of the aforesaid halogen from intermediate ester 9 or 12 or from intermediate amide 10 or 13, with an anion prepared by methods well known to one skilled in the art from a $C_1$-$C_6$alkyl-OH, an aryl($C_1$-$C_6$alkyl)-OH, a heterocycle($C_1$-$C_6$alkyl)-OH, a $C_1$-$C_6$ alkyl-SH, an aryl($C_1$-$C_6$alkyl)-SH, a heterocycle($C_1$-$C_6$alkyl)-SH, a $C_1$-$C_6$alkyl- NH$_2$, a (C$_1$-C$_6$alkyl)$_2$NH, or an aryl(C$_1$-C$_6$alkyl)-amine or a heterocycle(C$_1$-C$_6$alkyl)amine wherein said amine nitrogen is optionally substituted with C$_1$-C$_6$alkyl, provides, after thioarylation, a scheme 2 compound of formula (I) or formula (II) wherein R$_4$ is C$_1$-C$_6$alkoxy, aryl-(C$_1$-C$_6$alkoxy), heterocycle-(C$_1$-C$_6$alkoxy), C$_{1-6}$alkylthio, aryl-(C$_1$-C$_6$alkylthio), heterocycle-(C$_1$-C$_6$alkylthio), NR$_5$R$_6$ wherein R$_5$ is H or C$_1$-C$_6$alkyl and R$_6$ is C$_1$-C$_6$alkyl, or aryl(C$_1$-C$_6$alkyl)amino or heterocycle(C$_1$-C$_6$alkyl)amino wherein said amine nitrogen is optionally substituted with C$_1$-C$_6$alkyl.

As shown in scheme 2, optional step f, the nitrogen of the pyrrole ring of a compound of formula (I) or formula (II), wherein R$_1$ is H, is N-alkylated by methods as described above for scheme 1, optional step d, to provide a scheme 2 compound of formula (I) or formula (II) wherein R$_1$ is C$_1$-C$_6$alkyl.

Additionally a compound of formula (I) or formula (II) of scheme 2 wherein R$_1$ is H or C$_1$-C$_6$alkyl and X is S, is optionally oxidized to a sulfone or a sulfoxide wherein X is S(O)$_n$ and n is 1 or 2, respectively, by methods well known to one skilled in the art, such as for example, treating a solution of said compound of formula (I) or formula (II) wherein X is S with H$_2$O$_2$ and Na$_2$CO$_3$. Alternatively, compound 10 or 13 of scheme 2 is treated with an arylsulfonyl chloride, an arylsulfinyl chloride, a heterocyclesulfonyl chloride or a heterocyclesulfinyl chloride (used in place of the diaryldisulfide or diheterocycledisulfide) as described in step e above, to provide a scheme 2 compound of formula (I) or formula (II) wherein X is S(O)$_n$, n is 1 or 2 and R$_3$ is aryl or heterocycle.

Scheme 3

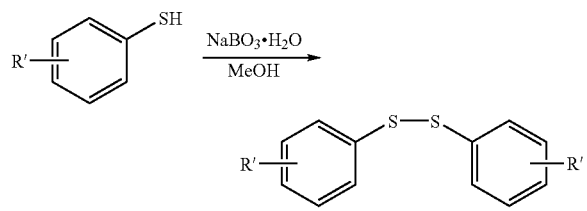

As shown in scheme 3, diaryldisulfides are prepared by treating a solution of an arylsulfide in a suitable organic solvent, such as for example methanol, with an aqueous solution of sodium perborate and allowing the mixture to stand for about 12 hours to about 24 hours at ambient temperature. The diaryldisulfide may be isolated and purified by methods as are well known to one skilled in the art. Diheterocycledisulfides such as for example bis(2-pyridinyl)disulfide are prepared in a similar manner. The arylsulfide and heterocyclesulfide are each optionally substituted as is defined above for "aryl" and "heterocycle".

All of the various embodiments of the compounds of this invention as disclosed herein can be used in the method for treating various diseases and disorders as described herein. As stated herein the compounds used in the method of this invention are capable of inhibiting the effects of casein kinase Iε.

One embodiment of this invention provides a method for treating a mood disorder or a sleep disorder. Another embodiment of the present invention provides a method for treating mood disorder wherein the mood disorder is a depressive disorder or a bipolar disorder. A further embodiment of the present invention provides a method for treating a depressive disorder wherein the depressive disorder is major depressive disorder. Another embodiment of the present invention provides a method for treating mood disorder wherein the mood disorder is bipolar disorder and the bipolar disorder is selected from the group from the group consisting of bipolar I disorder and bipolar II disorder. Another embodiment of the present invention provides a method for treating a sleep disorder. A further embodiment of the present invention provides a method for treating sleep disorder wherein the sleep disorder is a circadian rhythm sleep disorder. A further embodiment of the present invention provides a method for treating circadian rhythm sleep disorder wherein the circadian rhythm sleep disorder is selected from the group consisting of shift work sleep disorder, jet lag syndrome, advanced sleep phase syndrome and delayed sleep phase syndrome. One skilled in the art readily appreciates that the diseases and disorders expressly stated herein are not intended to be limiting but rather to illustrate the efficacy of the compounds of the present invention. Thus, it is to be understood that the compounds of the invention may be used to treat any disease or disorder ameliorated by the inhibition of casein kinase Iε.

In another embodiment of the present invention, pharmaceutical compositions comprising a pharmaceutically acceptable carrier and a compound of formula (I) or formula (II), or a stereoisomer, an enantiomer, a racemate or a tautomer of said compound; or a pharmaceutically acceptable salt thereof, are prepared in a manner well known to one skilled in the pharmaceutical arts. The carrier or excipient may be a solid, semisolid or liquid material which can serve as a vehicle or medium for the active ingredient. Suitable carriers or excipients are well known in the art. The pharmaceutical composition may be adapted for oral, inhalation, parenteral or topical use, and may be administered to the patient in the form of tablets, capsules, suspensions, syrups, aerosols, inhalants, suppositories, salves, powders, solutions and the like. As used herein, the term "pharmaceutical carrier" means one or more excipients. As described herein, the pharmaceutical compositions of the invention provide inhibition of casein kinase Iε and are thus useful for the treatment of diseases or disorders ameliorated by inhibition of casein kinase Iε

In preparing pharmaceutical compositions or formulations of the compounds of the present invention, care should be taken to ensure bioavailability of an effective therapeutic amount of the active compound or compounds by the selected route of administration, including oral, parenteral and subcutaneous routes. For example, effective routes of administration may include subcutaneous, intravenous, transdermal, intranasal, rectal, vaginal and the like routes including release from implants as well as injection of the active ingredient and/or composition directly into the tissue.

For oral administration, the compounds of the present invention can be formulated into solid or liquid preparations, with or without inert diluents or edible carriers, such as capsules, pills, tablets, troches, powders, solutions, suspensions or emulsions. The capsules, pills, tablets, troches and the like may also contain one or more of the following adjuvants: binders such as microcrystalline cellulose, gum tragacanth; excipients such as starch or lactose, disintegrating agents such as alginic acid, corn starch and the like; lubricants such as stearic acid, magnesium stearate or Sterotex®, (Stokely-Van Camp Inc., Indianapolis, Ind.) glidants such as colloidal silicon dioxide; sweetening agents such as sucrose or saccharin; and flavoring agents such as peppermint, methyl salicylate or fruit flavoring. When the dosage unit form is a capsule, it may also contain a liquid carrier such as polyethylene glycol or a fatty oil. Materials used should be pharmaceutically pure and nontoxic in the amounts used. Alternatively, the pharmaceutical compositions may be prepared in a form suitable for extended release to provide a therapeutic amount of a compound of formula (I) of the invention in a suitable once daily, once weekly or once monthly form using methods as are will known to one skilled in the art. For example, an erodible polymer containing the active ingredient may be envisaged.

For parenteral administration, the compounds of the present invention may be administered as injectable dosages of a solution or suspension of the compound in a physiologically acceptable diluent with a pharmaceutical carrier which can be a sterile liquid such as water-in-oil or without the addition of a surfactant and other pharmaceutically acceptable excipients. Illustrative oils which can be employed in the preparations are those of petroleum, animal, vegetable or synthetic origin such as, for example, peanut oil, soybean oil and mineral oil. In general, water, saline, aqueous dextrose and related sugar solutions, ethanol and glycols, such as propylene glycol are preferred liquid carriers, particularly for injectable solutions. The parenteral preparation can be enclosed in ampoules, disposable syringes or multiple dose vials made of inert plastic or glass.

The solutions or suspensions described above may also include one or more of the following adjuvants: sterile diluents such as water for injection, saline solution, fixed oils, polyethylene glycols, glycerin, propylene glycol or other synthetic solvents, antibacterial agents such as ascorbic acid or sodium bisulfite; chelating agents such as ethylenediaminetetra-acetic acid; buffers such as acetates, citrates or phosphates and agents for the adjustment of tonicity such as sodium chloride or dextrose.

The compounds of the present invention can be administered in the form of a cutaneous patch, a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones. Suitable pharmaceutical carriers and formulation techniques are found in standard texts, such as Remington: The Science and Practice of Pharmacy, 19$^{th}$ edition, Volumes 1 and 2, 1995, Mack Publishing Co., Easton, Pa., U.S.A., which is herein incorporated by reference.

In the treatment of various diseases, disorders and conditions as described herein, a suitable dosage level is about 0.01 mg/kg per day to about 250 mg/kg per day, preferably about 0.05 mg/kg per day to about 100 mg/kg per day, and especially about 0.05 mg/kg per day to about 40 mg/kg per day. The compounds of the present invention may be administered on a regimen of 1 to 4 times per day and as dictated by the nature of the disease, disorder or condition to be treated.

The contents of all publications and patents discussed herein are hereby incorporated herein by reference. It will also be appreciated that every suitable combination of the respective elements of the present invention may be interchanged with one or more other similar, suitable components known in the art and changed in minor, non-functional respects. These additional embodiments of the invention are also regarded as falling within the scope of the claims herein. The examples detailed below are provided to better describe and more specifically set forth the elements and mechanics/operation of the present invention with reference to the drawings, but for obvious reasons cannot describe all of them. It is to be recognized that said examples therefore are for illustrative purposes only however, and should not be interpreted as limiting the spirit and scope of the invention as later recited by the claims that follow.

EXAMPLES

The following examples are intended to serve for the illustration of the invention in greater detail, without restricting the breadth of the invention in any manner. Tables 1, 2, 3 and 4 provide summaries of the example compounds that are prepared herein.

Unless otherwise noted, all starting materials, reagents and solvents were obtained from commercial suppliers and used without further purification. All reactions were run under inert atmosphere with dry reagents and solvents. Flash chromatography was carried out using silica gel 60 (35-70 μm) according to the literature procedure (Still, W. C.; Kahn, M; Mitra, A. J. Org. Chem. 1978 43, 2923) or a variation of this method using a commercially available silica gel cartridge (for example Isco Redi Sep). Thin layer chromatography (TLC) was performed on glass-backed, silica gel 60F-254 plates (EM) coated to a thickness of 0.25 mm. The plates were eluted with solvent systems (v/v) as described, and visualized by iodine vapor, UV light, or a staining reagent such as KMnO$_4$ solution.

$^1$H NMR spectra were recorded on a Varian Gemini 300, Unity 300, Unity 400, or Unity 500 spectrometers with chemical shifts (δ) reported in ppm relative to tetramethylsilane (0.00 ppm) or chloroform (7.26 ppm) as a reference. Liquid chromatography with mass spectral analysis (LCMS) was recorded on a Micromass LCTAPI LC-TOF (time of flight) Mass Spectrometer and Masslynx Data System. Ionization mode=electrospray (esi), values were determined for the protonated molecular ions (M$^+$+1) using a Synergi 2U HYDRO-RP 20×4 mm column, eluting with 0.1% TFA in water/acetonitrile.

4H-Thieno[3,2-b]pyrrole-5-carboxylic acid ethyl ester and 6H-thieno[2,3-b]pyrrole-5-carboxylic acid ethyl ester were prepared as described in Eras, J.; Galvez, C.; Garcia, F. Journal of Heterocyclic Chemistry (1984), 21(1), 215-17. Ethyl esters of 4H-pyrrolo[2,3-d]thiazole-5-carboxylic acid, 6H-pyrrolo[3,2-d]thiazole-5-carboxylic acid, and 2-methyl-4H-pyrrolo[3,2-d]thiazole-5-carboxylic acid were prepared in the same fashion as described in WO9940914. 2-Alkylthio-, 2-arylalkylthio- and 2-alkyl-substituted pyrrolo[2,3-d]imidazole-5-carboxylic acid esters can be prepared as described in Shafiee, A. and Hadizadeh, F., J. of Heterocyclic Chemistry (1997), 34, 549-550 and in Shafiee, A.; Shahbazi Mojarrad, J.; Jalili, M. A.; Adhami, H. R. and Hadizadeh, F. Journal of Heterocyclic Chemistry, 39, 367-373. 4-Thiazolecarboxaldehyde, 5-thiazolecarboxaldehyde and 2-methyl-5-thiazolecarboxaldehyde were commercially obtained. 1,4-Dihydro-4-methylpyrrolo[3,2-b]pyrrole-2-carboxylic acid ethyl ester is prepared as described by H. Hemetsberger and D. Knittel, Monatsh. Chem. (1972) 103(1), 194-204.

Preparation of
2-bromo-6H-pyrrolo[3,2-d]thiazole-5-carboxylic
acid ethyl ester

2-Azido-3-(2-bromo-4-thiazolyl)propenoic acid
ethyl ester

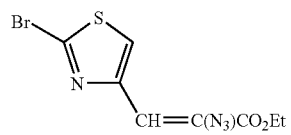

Add slowly to a solution of potassium ethoxide (30 ml, 24% w:w, 3 eq. of EtOK) a slurry of 2-bromo-4-thiazolylcarboxyaldehyde (3.87 gm, 30 mol) and 2-azidoacetate ethyl ester (11.5 gm, 3 esq.) in a mixed solvent of ethanol (150 ml) DMF (5 ml) and methylene chloride (DCM, 20 ml) at 0° C. over 15-20 minutes. Stir the final mixture overnight (18 hr) at room temperature, quench the reaction with ammonium chloride and remove the ethanol (~50 ml) on a rotary evaporator. Extract the aqueous mixture with DCM (3×250 ml portions), wash the organic phase with brine and dry over MgSO$_4$. Filter and concentrate the filtrate, and purify the crude mixture (12.2 gm) by flash chromatography [ISCO, SiO$_2$, 120 gm cartridge, elute with methanol: DCM (0-5%)] to afford the title compound (3.6 gm, 45%).

LCMS: retention time=3.68 min, (M$^+$)=302.98

2-Bromo-6H-pyrrolo[3,2-d]thiazole-5-carboxylic acid ethyl ester

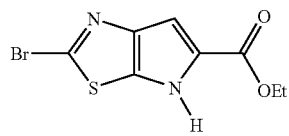

Add dropwise to hot xylene (130° C., 4 ml) a solution of 2-azido-3-(2-bromo-4-thiazolyl)propenoic acid ethyl ester (60 mg, 0.2 mmol) in DCM (1 ml). Heat the mixture for one hour, then cool to room temperature, deposit the mixture on a pad of silica gel and elute with heptane:DCM (50%-100%) to provide the title compound (14 mg).

LCMS: retention time=3.04 min, (M$^+$)=274.92.

Preparation of 4H-Pyrrolo[2,3-d]thiazole-5-carboxylic acid ethyl ester

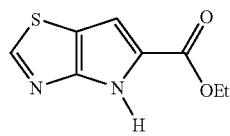

Prepare 4H-pyrrolo[2,3-d]thiazole-5-carboxylic acid ethyl ester from 4-thiazolylcarboxyaldehyde in a similar manner as described above for the preparation of 2-bromo-6H-pyrrolo[3,2-d]thiazole-5-carboxylic acid ethyl ester from 2-bromo-4-thiazolylcarboxyaldehyde.

Preparation of 2-bromo-6H-pyrrolo[3,2-d]thiazole-5-carboxylic acid

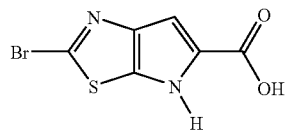

Add KOH (1.07 gm, 2 eq) to a mixture of 2-bromo-6H-pyrrolo[3,2-d]thiazole-5-carboxylic acid ethyl ester (2.6 gm, 9.38 mmol) in THF (15 ml) and water (20 ml), and then heat at 100° C. for 1 hr. Allow to stand overnight at room temperature and collect the crystalline solids by filtration (weight 1.7 gm). Concentrate the aqueous solution in vacuo, and combine the residue with the previously isolated crystalline solid. Acidify with acetic acid in methanol to provide the title compound (2.31 g).

LCMS: retention time=2.35 min, (M$^+$)=246.93

Preparation of 6H-Pyrrolo[3,2-d]thiazole-5-carboxylic acid

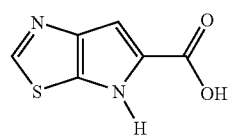

Prepare 6H-pyrrolo[3,2-d]thiazole-5-carboxylic acid by hydrolysis of 6H-pyrrolo[3,2-d]thiazole-5-carboxylic acid ethyl ester in a similar manner as described above for the preparation of 2-bromo-6H-pyrrolo[3,2-d]thiazole-5-carboxylic acid from 2-bromo-6H-pyrrolo[3,2-d]thiazole-5-carboxylic acid ethyl ester.

Preparation of Carboxylic Acid Amide Intermediates

4H-Thieno[3,2-b]pyrrole-5-carboxylic acid amide

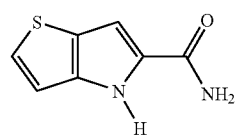

Add to 4H-thieno[3,2-b]pyrrole-5-carboxylic acid ethyl ester (1.74 gm, 8.9 mmol) and 7M ammonia in methanol (100 ml) in a steel bomb a chip of lithium hydroxide (0.1 gm). Seal the bomb and heat to 100° C. for 16 hrs. Cool to room temperature, and concentrate to remove the volatiles. Purify the crude product via flash chromatography (ISCO, silica cartridge, 40 gm, elute with methanol 0-5% in methylene chloride) to provide the title compound (560 mg, 38%) as an off-white solid.

LCMS: retention time=2.08 min, (M$^+$)=166.02

1H NMR (300 MHz, DMSO-D6) δ ppm 6.95 (d, J=5.25 Hz, 1H) 7.05-7.08 (m, 1H) 7.11 (br s, 1H) 7.37 (d, J=5.25 Hz, 1H) 7.68 (br s, 1H) 11.64 (s, 1H)

The following amides were also prepared by the above procedure:

6H-Pyrrolo[3,2-d]thiazole-5-carboxylic acid amide (LCMS: retention time=1.63 min, (M$^+$+H)=168.00)

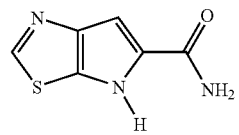

2-Methyl-6H-pyrrolo[3,2-d]thiazole-5-carboxylic acid amide (LCMS: retention time=1.28 min, (M++H)=182)

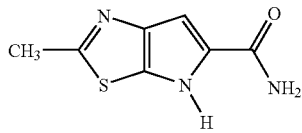

2-Bromo-6H-pyrrolo[3,2-d]thiazole-5-carboxylic acid amide

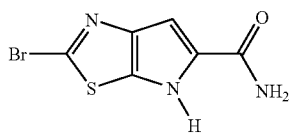

Add to a solution of 2-bromo-6H-pyrrolo[3,2-d]thiazole-5-carboxylic acid (2.53 gm, 10 mmol) in DMF (45 ml), DIEA (diisopropylethylamine, 10 ml, 6 eq), EDC (1-(3-dimethylaminopropyl)-3-ethylcarbodiimide HCl, 5.0 gm, 3.5 eq); HOBT (1-hydroxybenzotriazole, 1.91 gm, 14 mmol, 1.4 eq) and NH$_4$Cl (2.25 gm, 42.0 mmol). Stir the mixture at room temp for 6 hr and monitor by LC-MS. When complete, dilute the mixture with ethyl acetate, and wash with water and brine. Collect the solid by filtration (2.21 gm) and purify by chromatography on silica gel (ISCO silica cartridge, 4 gm, elute with methanol (10-40%) in methylene chloride) to afford the title compound (550 mg).

LCMS: retention time=2.11 min, (M+)=245.98

6H-Pyrrolo[3,2-d]thiazole-5-carboxylic acid amide

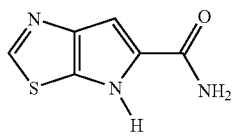

Prepare 6H-pyrrolo[3,2-d]thiazole-5-carboxylic acid amide by amination of 6H-pyrrolo[3,2-d]thiazole-5-carboxylic acid in a similar manner as described above for the preparation of 2-bromo-6H-pyrrolo[3,2-d]thiazole-5-carboxylic acid amide from 2-bromo-6H-pyrrolo[3,2-d]thiazole-5-carboxylic acid.

General Preparation of Diaryldisulfides and Diheterocycledisulfides

Add to a solution of the unsubstituted or appropriately substituted arylthiol (17.2 millimole, 1.0 equivalent) and MeOH (30 mL), a solution of sodium perborate (22 millimole) and water (20 mL) with stirring, and then allow the reaction to stand at rt overnight. Collect the solid by filtration and wash with methanol to give the desired diaryldisulfide. Other disulfides including diheterocycledisulfides (e.g. bis(2-thienyl)disulfide) can be prepared in a similar manner as described for the preparation of the desired diaryldisulfides.

Methods for Thioarylation of the Pyrrole Moiety

Method 1: 6-Phenylsulfanyl-4H-thieno[3,2-b]pyrrole-5-carboxylic acid amide (Ia)

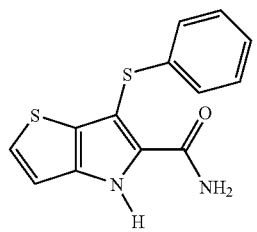

Treat 4H-thieno[3,2-b]pyrrole-5-carboxylic acid amide (75 mg, 0.45 mmol) with NaH (45 mg, 60% in oil, 1.12 mmol, 2.5 eq) in N,N-dimethylformamide (1.3 ml) at room temperature under nitrogen for 35 minutes. Add diphenyldisulfide (137 mg, 1.4 eq) and heat the mixture at 70° C. overnight. Dilute the mixture with brine (2 ml) and extract with ethyl acetate. Concentrate the ethyl acetate solution to give an oil and purify by chromatography on silica gel (ISCO silica cartridge, 4 gm, elute with methanol 0-10% in methylene chloride) to afford the title compound (55 mg).

LCMS: retention time=3.03 min, (M++H)=275.01

1H NMR (300 MHz, CDCl$_3$) δ ppm 5.94 (s, 1H) 7.03 (d, J=5.25 Hz, 1H) 7.14-7.27 (m, 6H) 7.79 (br s, 1H) 10.79 (br s, 1H)

Method 2: 6-(3-Fluorophenylsulfanyl)-4H-thieno[3,2-b]pyrrole-5-carboxylic acid amide (Ib)

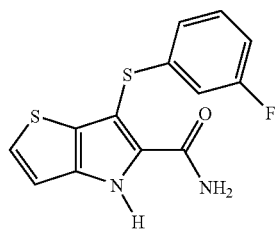

Add 4H-thieno[3,2-b]pyrrole-5-carboxylic acid amide (60 mg, 0.36 mmol) to a mixture of bis(3-fluorophenyl)disulfide, (150 mg, 0.51 mmol) and cesium carbonate (120 mg, 1 eq.) in DMF (2.5 ml), and then heat at 95° C. for 3 hrs. Follow the reaction by TLC. When complete, dilute the reaction mixture with ethyl acetate (15 ml) and wash with brine (25 ml). Dry the organic solution, concentrate to afford a crude oil and purify the oil by chromatography on silica gel (ISCO silica cartridge, 4 gm, elute with methanol 0-10% in methylene chloride) to provide the title compound (81 mg).

LCMS: retention time=3.47 min, (M++H)=293

1H NMR (300 MHz, CDCl$_3$) δ ppm 5.67 (s, 1H), 6.82-6.90 (m, 2H), 6.96 (ddd, J=7.87, 1.50, 1.37 Hz, 1H), 7.03 (d, J=5.25 Hz, 1H), 7.17-7.24 (m, 1H), 7.31 (d, J=5.25 Hz, 1H), 7.70 (s, 1H), 9.96 (s, 1H)

Method 3: 4-(Pyridin-2-ylsulfanyl)-6H-thieno[2,3-b]pyrrole-5-carboxylic acid amide (IIa)

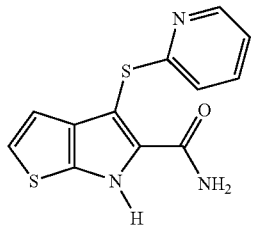

Treat 6H-thieno[2,3-b]pyrrole-5-carboxylic acid amide (57 mg, 0.34 mmol) with NaH (19 mg, 0.78 mmol, 2.3 eq) in N,N-dimethylformamide (1 ml) at room temperature, under nitrogen for 45 minutes. Add 2,2'-dipyridyldisulfide (106 mg, 1.4 eq) and stir the mixture overnight at ambient temperature. Dilute the mixture with water and extract with ethyl acetate. Concentrate the ethyl acetate solution to give a residue which is purified by flash chromatography (ISCO, silica cartridge, elute with 5% methanol in methylene chloride (+1% 7N ammonia in methanol) to provide the title compound (32 mg, 32%).

LCMS: retention time=2.53 min, $(M^++H)$=276.022

Method 4: 4-(Phenylsulfanyl)-6H-thieno[2,3-b]pyrrole-5-carboxylic acid amide (IIb)

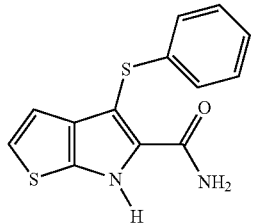

Treat 6H-thieno[2,3-b]pyrrole-5-carboxylic acid amide (50 mg, 0.30 mmol) in N,N-dimethylformamide (0.5 ml) with NaH (29 mg, 60% in oil, 0.75 mmol, 2.5 eq) at room temperature, under nitrogen for 45 minutes. Add diphenyl disulfide (92 mg, 0.4 mmol 1.4 eq) and stir the mixture at 60° C. overnight. Increase the temperature to 100° C. for 5 hours and cool to room temperature. Dilute the reaction with water and ethyl acetate* whereupon the title compound crystallizes from solution. Collect the product by filtration and dry under vacuum, to afford the title compound (28 mg).

LCMS: retention time=3.068 min, $(M^++H)$=275.024

*In some cases (see tables 1 and 2, synthesis method column) where method 4 was employed, the compounds did not crystallize. In this situation, separate the ethyl acetate portion and concentrate to give a crude residue and purify the residue by flash chromatography (ISCO, silica cartridge, eluted with 10% methanol in methylene chloride (+1% 7N ammonia in methanol) to provide the desired compound.

Method 5: 2,6-Bis-phenylsulfanyl-4H-pyrrolo[3,2-d]thiazole-5-carboxylic acid amide (IIq)

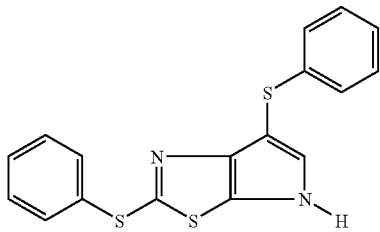

Add diphenyldisulfide (93 mg, 0.43 mmol, 1.25 eq) to a mixture of 2-bromo-4H-pyrrolo[3,2-d]thiazole-5-carboxylic acid amide (85 mg, 0.34 mmol) and cesium carbonate (140 mg, 1.25 eq) in DMF (4 ml). Heat the mixture at 100° C. for 16 hours. Remove the DMF under reduced pressure and partition the residue between water and ethyl acetate. Wash the organic phase with brine, and then dry and filter the organic phase. Add the filtrate to a flask containing a small amount of silica gel (about 0.5 gm) and evaporate the solvent to provide the crude product adsorbed onto the silica gel. Place the silica gel on top of a small column containing about 4 gm of silica gel and elute with 0-10% of MeOH in DCM to provide 8 mg (6.5%) of the title compound.

LCMS: retention time=3.30 min, $(M^+)$=383.02

TABLE 1

Compounds of Formula (I)

(M is S)

| Example No. | $R_1$ | $R_2$ | $R_3X$ | $R_4$ | L | Synthesis Method |
|---|---|---|---|---|---|---|
| Ia | H | $NH_2$ | $C_6H_5S$ | H | CH | 1 |
| Ib | H | $NH_2$ | 3-F-$C_6H_4$S | H | CH | 1 |
| Ic | H | $NH_2$ | 4-Cl-$C_6H_4$S | H | CH | I |
| Id | H | $NH_2$ | 2-$NH_2$-$C_6H_4$S | H | CH | I |
| Ie | H | $NH_2$ | 2-pyridinylS | H | CH | I |
| If | H | $NH_2$ | 4-$CH_3$—$C_6H_4$S | H | CH | I |
| Ig | H | $NH_2$ | 2-thienylS | H | CH | 2 |
| Ih | H | $NH_2$ | 3,5-$(Cl)_2$—$C_6H_3$S | H | CH | 2 |
| Ii | H | $NH_2$ | 4-pyridinylS | H | CH | 2 |
| Ij | H | $NH_2$ | 3-$CH_3$—$C_6H_4$S | H | CH | 2 |
| Ik | H | $NH_2$ | 2-$CH_3$—$C_6H_4$S | H | CH | 2 |
| Il | H | $NH_2$ | 2,3-$(Cl)_2$—$C_6H_3$S | H | CH | 2 |
| Im | H | $NH_2$ | 2,5-$(Cl)_2$—$C_6H_3$S | H | CH | 2 |
| In | H | $NH_2$ | 2-$C_2H_5$—$C_6H_4$S | H | CH | 2 |
| Io | H | $NH_2$ | 3-Br—$C_6H_4$S | H | CH | 2 |
| Ip | H | $NH_2$ | 3,5-$(CH_3)_2$—$C_6H_3$S | H | CH | 2 |
| Iq | H | $NH_2$ | 3-$CH_3$O—$C_6H_4$S | H | CH | 2 |
| Ir | H | $NH_2$ | 2-$CH_3$O—$C_6H_4$S | H | CH | |
| Is | H | $NH_2$ | 2-$CF_3$—$C_6H_4$S | H | CH | 2 |
| It | H | $NH_2$ | 2-F—$C_6H_4$S | H | CH | 2 |
| Iu | H | $NH_2$ | 3-$CF_3$O—$C_6H_4$S | H | CH | 2 |
| Iv | H | $NH_2$ | $C_6H_5$S | H | N | 4 |
| Iw | H | $NH_2$ | 3-F—$C_6H_4$S | H | N | 4* |
| Ix | H | $NH_2$ | 2-pyridinylS | H | N | 4 |

*See footnote accompanying method 4.

TABLE 2

Compounds of Formula (II)
(M is S)

$$\text{(II)}$$

| Example No. | R$_1$ | R$_2$ | R$_3$X | R$_4$ | L | Synthesis Method |
|---|---|---|---|---|---|---|
| IIa | H | NH$_2$ | 2-pyridinylS | H | CH | 3 |
| IIb | H | NH$_2$ | C$_6$H$_5$S | H | CH | 4 |
| IIc | H | NH$_2$ | 3-F-C$_6$H$_4$S | H | CH | 4* |
| IId | H | NH$_2$ | 4-pyridinylS | H | CH | 1 |
| IIe | H | NH$_2$ | 3,5-(Cl)$_2$—C$_6$H$_3$S | H | CH | 1 |
| IIf | H | NH$_2$ | 2-thienylS | H | CH | 1 |
| IIg | H | NH$_2$ | 3-Br—C$_6$H$_4$S | H | CH | 2 |
| IIh | H | NH$_2$ | 3-CH$_3$O—C$_6$H$_4$S | H | CH | 2 |
| IIi | H | NH$_2$ | 2-CH$_3$O—C$_6$H$_4$S | H | CH | 2 |
| IIj | H | NH$_2$ | 3-Cl—C$_6$H$_4$S | H | CH | 2 |
| IIk | H | NH$_2$ | 3-CH$_3$—C$_6$H$_4$S | H | CH | 2 |
| IIl | H | NH$_2$ | C$_6$H$_5$S | CH$_3$ | N | 2 |
| IIm | H | NH$_2$ | 3-CH$_3$O—C$_6$H$_4$S | CH$_3$ | N | 2 |
| IIn | H | NH$_2$ | 3-F—C$_6$H$_4$S | CH$_3$ | N | 2 |
| IIo | H | NH$_2$ | 3-Cl—C$_6$H$_4$S | CH$_3$ | N | 2 |
| IIp | H | NH$_2$ | 3-CF$_3$O—C$_6$H$_4$S | CH$_3$ | N | 2 |
| IIq | H | NH$_2$ | C$_6$H$_5$S | C$_6$H$_5$S | N | 5 |
| IIr | H | NH$_2$ | 3-CH$_3$O—C$_6$H$_4$S | 3-CH$_3$O—C$_6$H$_4$S | N | 5 |
| IIs | H | NH$_2$ | C$_6$H$_5$S | H | N | 2 |
| IIt | H | NH$_2$ | 3-CH$_3$O—C$_6$H$_4$S | H | N | 2 |

\* See footnote accompanying method 4.

TABLE 3

Spectral Data for Compounds of Formula (I)
(M is S)

| Example No. | Compound Name | MS: Obs. Ion Mass* (amu) | MS: Retention time (min) |
|---|---|---|---|
| Ia | 6-Phenylsulfanyl-4H-thieno[3,2-b]pyrrole-5-carboxylic acid amide | 275.011 | 3.034 |
| Ib | 6-(3-Fluorophenyl-sulfanyl)-4H-thieno[3,2-b]pyrrole-5-carboxylic acid amide | 293 | 3.47 |
| Ic | 6-(4-Chlorophenyl-sulfanyl)-4H-thieno[3,2-b]pyrrole-5-carboxylic acid amide | 308.967 | 3.268 |
| Id | 6-(2-Aminophenyl-sulfanyl)-4H-thieno[3,2-b]pyrrole-5-carboxylic acid amide | 290.025 | 2.668 |
| Ie | 6-(Pyridin-2-ylsulfanyl)-4H-thieno[3,2-b]pyrrole-5-carboxylic acid amide | 276 | 2.57 |
| If | 6-p-Tolylsulfanyl-4H-thieno[3,2-b]pyrrole-5-carboxylic acid amide | 289.024 | 3.218 |
| Ig | 6-(Thiophen-2-yl-sulfanyl)-4H-thieno[3,2-b]pyrrole-5-carboxylic acid amide | 281.02 | 2.97 |
| Ih | 6-(3,5-Dichlorophenylsulfanyl)-4H-thieno[3,2-b]pyrrole-5-carboxylic acid amide | 342.96 | 3.55 |
| Ii | 6-(Pyridin-4-ylsulfanyl)-4H-thieno[3,2-b]pyrrole-5-carboxylic acid amide | 276 | 1.39 |
| Ij | 6-m-Tolylsulfanyl-4H-thieno[3,2-b]pyrrole-5-carboxylic acid amide | 287 | 2.71 |
| Ik | 6-o-Tolylsulfanyl-4H-thieno[3,2-b]pyrrole-5-carboxylic acid amide | 289 | 2.69 |
| Il | 6-(2,3-Dichloro-phenylsulfanyl)-4H-thieno[3,2-b]pyrrole-5-carboxylic acid amide | 342.95 | 3.57 |
| Im | 6-(2,5-Dichloro-phenylsulfanyl)-4H-thieno[3,2-b]pyrrole-5-carboxylic acid amide | 342.95 | 3.5 |
| In | 6-(2-Ethylphenylsulfanyl)-4H-thieno[3,2-b]pyrrole-5-carboxylic acid amide | 303.06 | 3.45 |
| Io | 6-(3-Bromo-phenylsulfanyl)-4H-thieno-[3,2-b]pyrrole-5-carboxylic acid amide | 352.932 | 3.4 |
| Ip | 6-(3,5-Dimethylphenylsulfanyl)-4H-thieno[3,2-b]pyrrole-5-carboxylic acid amide | 303.05 | 3.47 |
| Iq | 6-(3-Methoxy-phenylsulfanyl)-4H-thieno[3,2-b]pyrrole-5-carboxylic acid amide | 305.03 | 3.17 |
| Ir | 6-(2-Methoxy-phenylsulfanyl)-4H-thieno[3,2-b]pyrrole-5-carboxylic acid amide | 305.36 | 3.13 |
| Is | 6-(2-Trifluoromethyl-phenylsulfanyl)-4H-thieno[3,2-b]pyrrole-5-carboxylic acid amide | 343.01 | 3.37 |
| It | 6-(2-Fluoro-phenylsulfanyl)-4H-thieno[3,2-b]pyrrole-5-carboxylic acid amide | 293.02 | 3.15 |
| Iu | 6-(3-Trifluoromethoxy-phenylsulfanyl)-4H-thieno[3,2-b]pyrrole-5-carboxylic acid amide | 359.008 | 3.47 |
| Iv | 6-Phenylsulfanyl-4H-pyrrolo[2,3-d]thiazole-5-carboxylic acid amide | 274 | 3.052 |
| Iw | 6-(3-Fluoro-phenylsulfanyl)-4H-pyrrolo[2,3-d]thiazole-5-carboxylic acid amide | 294.013 | 2.851 |
| Ix | 6-(Pyridin-2-ylsulfanyl)-4H-pyrrolo[2,3-d]thiazole-5-carboxylic acid amide | 277.035 | 2.334 |

*Ion type is M + H unless otherwise noted.

TABLE 4

Spectral Data for Compounds of Formula (II)
(M is S)

| Example No. | Compound Name NMR (CDCl$_3$) | MS: Obs. Ion Mass* (amu) | MS: Retention time (min) |
|---|---|---|---|
| IIa | 4-(pyridin-2-ylsulfanyl)-6H-thieno[2,3-b]pyrrole-5-carboxylic acid amide | 276.022 | 2.53 |
| IIb | 4-(phenylsulfanyl)-6H-thieno[2,3-b]pyrrole-5-carboxylic acid amide | 275.024 | 3.068 |
| IIc | 6-(3-Fluorophenyl-sulfanyl)-6H-thieno[2,3-b]pyrrole-5-carboxylic acid amide | 276 | 3.43 |
| IId | 4-(Pyridin-4-ylsulfanyl)-6H-thieno[2,3-b]-pyrrole-5-carboxylic acid amide | 276.1 | 1.45 |
| IIe | 4-(3,5-Dichlorophenyl-sulfanyl)-6H-thieno[2,3-b]pyrrole-5-carboxylic acid amide | 325.9 | 2.98 |

TABLE 4-continued

Spectral Data for Compounds of Formula (II) (M is S)

| Example No. | Compound Name NMR (CDCl$_3$) | MS: Obs. Ion Mass* (amu) | MS: Retention time (min) |
|---|---|---|---|
| IIf | 4-(Thiophen-2-yl-sulfanyl)-6H-thieno[2,3-b]pyrrole-5-carboxylic acid amide | 264 | 2.43 |
| IIg | 4-(3-Bromophenyl-sulfanyl)-6H-thieno[2,3-b]pyrrole-5-carboxylic acid amide | 352.9 | 4.31 |
| IIh | 4-(3-Methoxyphenyl-sulfanyl)-6H-thieno[2,3-b]pyrrole-5-carboxylic acid amide | 305 | 3.44 |
| IIi | 4-(2-Methoxyphenyl-sulfanyl)-6H-thieno[2,3-b]pyrrole-5-carboxylic acid amide | 305 | 3.56 |
| IIj | 4-(3-Chlorophenyl-sulfanyl)-6H-thieno[2,3-b]pyrrole-5-carboxylic acid amide<br>1H NMR (300 MHz,) δ ppm 2.30 (s, 3H), 5.70 (br s, 1H), 6.89 (d, J = 5.25 Hz, 1H), 6.94-7.06 (m, 4H), 7.14 (t, J = 7.62 Hz, 1H), 7.87 (br s, 1H), 10.28 (br s, 1H) | 309.2 | 3.47 |
| IIk | 4-(3-Methylphenyl-sulfanyl)-6H-thieno[2,3-b]pyrrole-5-carboxylic acid amide | 289 | 4.1 |
| Ill | 2-Methyl-6-phenyl-sulfanyl-4H-pyrrolo[3,2-d]thiazole-5-carboxylic acid amide | 290.04 | 2.8 |
| IIm | 6-(3-Methoxyphenyl-sulfanyl)-2-methyl-4H-pyrrolo[3,2-d]thiazole-5-carboxylic acid amide<br>1H NMR (300 MHz,) δ ppm 2.75 (s, 3H), 3.71 (s, 3H), 5.69 (br s, 1H), 6.64-6.68 (m, 1H), 6.72-6.77 (m, 2H), 7.12 (t, J = 7.66 Hz, 1H), 7.86 (br s, 1H), 10.35 (br s, 1H) | 320.05 | 2.69 |
| IIn | 6-(3-Fluorophenyl-sulfanyl)-2-methyl-4H-pyrrolo[3,2-d]thiazole-5-carboxylic acid amide | 308.04 | 2.72 |
| IIo | 6-(3-Chlorophenyl-sulfanyl)-2-methyl-4H-pyrrolo[3,2-d]thiazole-5-carboxylic acid amide<br>1H NMR (300 MHz,) δ ppm 2.77 (s, 3H), 5.72 (br s, 1H), 7.03-7.18 (m, 4H), 7.76 (br s, 1H), 10.41 (br s, 1H) | 323.99 | 2.82 |
| IIp | 6-(3-Trifluoromethoxy-phenylsulfanyl)-2-methyl-4H-pyrrolo[3,2-d]thiazole-5-carboxylic acid amide | 374.02 | 3 |
| IIq | 2,6-Bis-phenylsulfanyl-4H-pyrrolo[3,2-d]thiazole-5-carboxylic acid amide | 384.05 | 3.3 |
| IIr | 2,6-Bis-(3-methoxy-phenylsulfanyl)-4H-pyrrolo[3,2-d]thiazole-5-carboxylic acid amide | 444.08 | 3.33 |
| IIs | 6-Phenylsulfanyl-4H-pyrrolo[3,2-d]thiazole-5-carboxylic acid amide | 275.98 | 2.77 |
| IIt | 6-(3-Methoxyphenyl-sulfanyl)-4H-pyrrolo[3,2-d]thiazole-5-carboxylic acid amide<br>1H NMR (300 MHz,) δ ppm 3.71 (s, 3H), 5.83 (br s, 1H), 6.66-6.70 (m, 1H), 6.77-6.81 (m, 2H), 7.13 (t, J = 8.00 Hz, 1H), 7.96 (br s, 1H), 8.55 (br s, 1H), 10.63 (br s, 1H) | 306 | 2.77 |

*Ion type is M + H unless otherwise noted. For IIc, IIe, IIf observed ion type was (M + H)-NH$_3$

BIOLOGICAL EXAMPLES

Casein Kinase Epsilon $^{33}$P-ATP Filter Plate Assay for Screening CKIε Inhibitors Purpose: This assay measures the ability of compounds to inhibit the phosphorylation of the substrate casein by the enzyme casein kinase 1ε using an in vitro $^{33}$P-ATP filtration assay. Compounds are tested at five concentrations in duplicate in order to generate IC$_{50}$ values or % inhibition at a 10 micromolar concentration that are summarized in Table 4.

Materials:
Equipment:
Beckman Biomek 2000 Liquid Handling Robot
Beckman Multimek 96 Automated 96 Channel Pipettor
Millipore Vacuum Manifold Basic Kit # MAVM0960R
Titertek Multidrop Liquid Dispenser
Packard TopCount NXT Liquid Scintillation Counter
Plates:
Costar EIA/RIA Plate #9018
Falcon 96 well U bottom Polystyrene Plate #353910
Millipore Multiscreen 96 well Filtration Plates #MAPH-NOB50
Millipore Multiscreen TopCount Adapter Plates #SE3M203V6
Chemicals:
EGTA from SIGMA #E-3889
Casein (dephosphorylated) from SIGMA #C-4032
ATP from SIGMA #A-7699
DTT from Fisher Biotech #BP1725
Trichloroacetic Acid from SIGMA #T-6399
γ-$^{33}$P-ATP 1 mCi/37 MBq from Perkin Elmer Life Sciences #NEG-602H
Enzyme:
Casein Kinase 1ε final concentration 0.58 mg/ml obtained from fermentation and purification processes as are well known to one skilled in the art. The above are stored as 100 μL aliquots at minus 80° C.
Compounds:
Supply compounds for testing as frozen 10 mM compound stock dissolved in 100% DMSO.

Assay Conditions:
Final total assay volume per well is equal to 50 μL that one prepares as follows:
5 μL of diluted compound stock (10, 1, 0.1, 0.01 or 0.001 μM),
5 μL of dephosphorylated casein final concentration 0.2 μg/μL,
20 μL of CK1ε final concentration 3 ng/μL, and
20 μL of γ-$^{33}$P-ATP final concentration 0.02 μCi/μL mixed with cold ATP (10 μM final).

Methodology:
1. Prepare 500 mL of fresh assay buffer: 50 mM Tris pH 7.5, 10 mM MgCl$_2$, 2 mM DTT and 1 mM EGTA
2. Obtain compounds to be evaluated as 10 μL of 10 mM stock dissolved in 100% DMSO. Use a Biomek 2000 liquid handling robot, make serial dilutions to yield 10, 1, 0.1, 0.01 and 0.001 μM final compound dilutions added as 5 μL additions to Falcon U bottom plates. Typically test 8 compounds per 96 well plate with column 1 and 12 serving as control wells. A routine screening assay will consist of 32 compounds, which equals 4 assay plates.
3. Assay plate maps are set up according to the following pattern CK1ePlateMap.xls

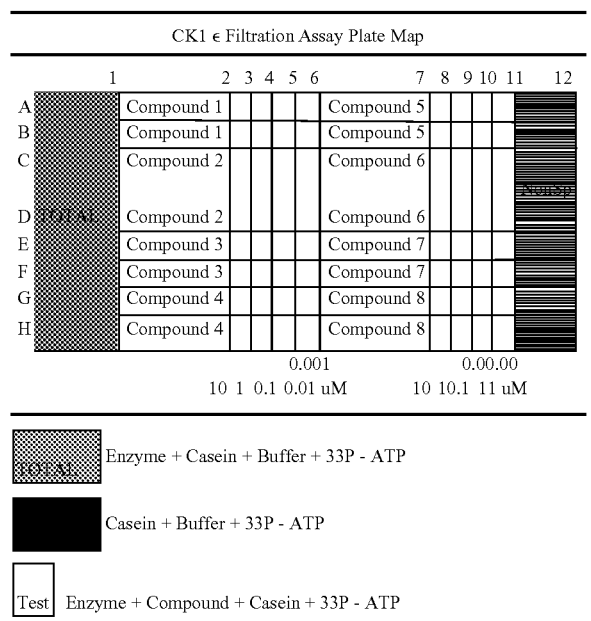

4. Add 5 μL of compound as indicated, then add 5 μL of dephosphorylated casein (dissolved in distilled H₂0)(0.2 μg/μL) and 20 μL CK1ε (3 ng/μL) to the appropriate wells.
5. Finally add 20 μL γ-$^{33}$P-ATP (0.02 μCi/μL)/10 μM cold ATP (equals approximately $2 \times 10^6$ CPM per well).
6. Vortex the Falcon U-Bottom assay plate containing the above 50 μL reaction volume and then incubate at room temperature for 2 hours.
7. At the end of 2 hours, stop the reaction by the addition of 65 μL of ice cold 2 mM cold ATP (made up in assay buffer) to the assay plates using a Beckman Multimek.
8. At the same time add 25 μL 100% ice cold TCA made up in distilled H₂0 to a matching number of Millipore MAPH filter plates.
9. Using a handheld 8-channel pipettor, transfer 100 μL of the reaction mixture from the Falcon U-Bottom Plate to the Millipore MAPH filter plates presoaked with TCA.
10. Mix the Millipore MAPH filter plates gently and allow to sit at room temperature for at least 30 minutes to precipitate the proteins.
11. After 30 minutes, place the filter plates on a Millipore vacuum manifold and filter at no more than 8 mm Hg as the MAPH filters tend to "air lock" at higher vacuum settings.
12. Wash the filter plates sequentially and filter with $2 \times 150$ μL 20% TCA, $2 \times 150$ μL 10% TCA and $2 \times 150$ μL 5% TCA (total of 6 washes per plate/900 μL per well).
13. Allow the plates to dry overnight at room temperature. The next day add 40 μL Packard Microscint-20 Scintillation Fluid per well using a Titertek Multidrop dispenser; seal the plates and count for 2 minutes/well in a Packard Topcount NXT Scintillation Counter (to provide CPM values/well).

Calculation:
1. Import Counts Per Minute (CPM) data into a proprietary data calculation and archiving database (Activity Base by IDBS version 5.0).
2. Column 1 for each plate reflects total phosphorylation activity of the enzyme in the absence of any inhibiting compound and thus represents 100%. Column 12 reflects any nonspecific phosphorylation/retained radioactivity activity in the absence of inhibiting compound and enzyme. Typically one observes approximately 1% of Total CPMs that are "nonspecific".
3. By determining the "total" and "nonspecific" CPMs for each plate, one is able to determine the % inhibition of the enzyme's ability to phosphorylate the substrate for each concentration of test compound. Use this % inhibition data to calculate an $IC_{50}$ value (concentration at which a compound is able to inhibit the enzyme activity by 50%) for a compound using a non-linear curve fit program contained with the Activitybase calculation protocol (DG0027-CK1-D-BL).
4. Kinetic studies have determined the $K_m$ value for ATP to be 21 μM in this assay system.

Casein Kinase 1δ Streptavidin Affinity Membrane Plate Assay for CK1δ Inhibitors

Purpose: To evaluate test compounds for CK1δ activity in Streptavidin Affinity Membrane (SAM) Biotin Capture Plate (Promega V7542)

Supplies and Reagents

HEPES Sigma # H3375 MW=238.3; β-Glycerol phosphate Sigma # G-9891 MW=216.0; EDTA 0.5M, pH 8.0 Gibco-BRL; Sodium orthovanadate ACROS # 205330500 MW=183.9; DTT (DL-dithiothreitol) Sigma # D-5545 MW=154.2; Magnesium Chloride ACROS #41341-5000 MW=203.3; ATP Sigma # A-7699 MW=551.1; γ$^{33}$P ATP NEN # NEG602H; Casein Kinase 1δ Sigma # C4455; Casein Kinase 1 substrate New England Peptide Biotin-RRKDLH-DDEEDEAMSITA MW=2470

Prepare Kinase Buffer (KB, 100 mL) as follows:

| | |
|---|---|
| 50 mM HEPES, pH 8.0 | 5 mL of 1 M stock |
| 10 mM MgCl | 1 mL of 1 M stock |
| 10 mM β-glycerophosphate | 1 mL of 1 M stock |
| 2.5 mM EDTA | 500 μL of 500 mM stock |
| 1 mM sodium orthovanadate | 100 μL of 1 M stock |
| 1 mM DTT | 100 μL of 1 M stock |
| water | 92.3 mL |

Prepare ATP Master Mix as follows:

Prepare 1 mL of a 1M ATP solution in water (1M ATP stock).
To 12 mL KB:
 Add 12 μL of 1M ATP solution, then
 Add 12 μL of $^{33}$P ATP (10 μCi/ul), NEG602H, Perkin Elmer Prepare the reaction plate and conduct the assay as follows:
1. Add 10 μL of KB per well with or without the test compound inhibitor to reaction plate wells
2. Add 60 μL of KB per well
3. Add 10 μL of 500 μM Peptide Substrate per well
4. Bring plate up to 37° C.
5. Add 10 μL of 1:10 dilution of CK1δ per well=0.42 μg or 0.68 units
6. Initiate the reaction with 10 μL of ATP Master Mix per well
7. Place the reaction plate in 37° C. incubator for 10 min.
8. Stop the reaction with 10 μL of 1M ATP. Transfer 20 μL to the SAM Plate and let stand 10 min at room temperature.

9. Wash three times with 100 μL of 2M NaCl solution, then three times with 100 μL of 2M NaCl and 1% $H_3PO_4$ solutions and then three times with 100 μL of water on a vacuum manifold.
10. Dry the filter plate under a lamp for 30 min.
11. Seal bottom of plate and add 20 μL of MicroScint 20
12. Read in TOPCOUNT Cellular Circadian Assay Experimental Procedures Cell culture: Split Mper1-luc Rat-1 fibroblasts (P2C4) cultures every 3-4 days (~10-20% confluence) onto 150 cm² vented polystyrene tissue culture flasks (Falcon # 35-5001) and maintain in growth media [EMEM (Cellgro #10-010-CV); 10% fetal bovine serum (FBS; Gibco #16000-044); and 50 I.U./mL penicillin-streptomycin (Cellgro #30-001-C1)] at 37° C. and 5% $CO_2$.

Stable transfection: Co-transfect Rat-1 fibroblast cultures at 30-50% confluence with vectors containing the Zeocin resistance selectable marker for stable transfection and an mPer-1 promoter-driven luciferase reporter gene. After 24-48 hours, split the cultures onto 96 well plates and maintain in growth media supplemented with 50-100 μg/mL Zeocin (Invitrogen #45-0430) for 10-14 days. Assess Zeocin-resistant stable transfectants for reporter expression by supplementing growth media with 100 μM luciferin (Promega #E1603) and assaying luciferase activity on a TopCount scintillation counter (Packard Model #C384V00). Synchronize Rat-1 clones expressing both Zeocin-resistance and mPer1-driven luciferase activity by 50% horse serum [HS (Gibco #16050-122)] serum shock and assess for circadian reporter activity. Select Mper1-luc Rat-1 fibroblasts clone P2C4 for compound testing.

Synchronization protocol: Plate Mper1-luc Rat-1 fibroblasts (P2C4) (40-50% confluence) onto opaque 96-well tissue culture plates (PerkinElmer #6005680) and maintain in growth media supplemented with 100 μg/mL Zeocin (Invitrogen #45-0430) until cultures reach 100% confluence (48-72 h). Synchronize cultures with 100 μL synchronization media [EMEM (Cellgro #10-010-CV); 100 I.U./mL penicillin-streptomycin (Cellgro #30-001-C1); 50% HS (Gibco #16050-122)] for 2 hours at 37° C. and 5% CO2. After synchronization, rinse cultures with 100 μL EMEM (Cellgro #10-010-CV) for 10 minutes at room temperature. After rinse, replace media with 300 μL CO2-independent media [CO2I (Gibco #18045-088); 2 mM L-glutamine (Cellgro #25-005-C1); 100 I.U./mL penicillin-streptomycin (Cellgro #30-001-C1); 100 μM luciferin (Promega #E1603)]. Add compounds to be tested for circadian effects to $CO_2$-independent media in 0.3% DMSO (final concentration). Seal cultures immediately with TopSeal-A film (Packard #6005185) and transfer for luciferase activity measurement.

Automated Circadian Reporter Measurement: After synchronization, maintain assay plates at 37° C. in a tissue culture incubator (Form a Scientific Model #3914). Estimate in vivo luciferase activity by measuring relative light output on a TopCount scintillation counter (Packard Model #C384V00). Transfer plates from incubator to reader using an ORCA robotic arm (Beckman Instruments) and SAMI-NT automated scheduling software (Version 3.3; SAGIAN/Beckman Instruments).

Data Analysis: Use Microsoft Excel and XLfit (Version 2.0.9; IDBS) to import, manipulate and graph data. Perform period analysis either by determining the interval between relative light output minima over several days or by Fourier Transform. Both methods produce nearly identical period estimation over a range of circadian periods. Report potency as $EC_{\square t+1h}$, which is the effective micromolar concentration that induces a 1 hour lengthening of period. Analyze the data by fitting a hyperbolic curve to the data expressed as period change (y-axis) versus the concentration of test compound (x-axis) in XLfit and interpolate the $EC_{\square t+1h}$ from this curve.

Rat Circadian Cycle Assay

This assay provides a means for assessing the effect of a test compound on circadian cycle in vivo. Use male Wistar rats (Charles River) with a starting body mass of 200-250 g. House each animal individually prior to testing in a controlled environment and maintain a thermoneutral ambient temperature of 24-28° C. under a 12/12 hour (h) light/dark cycle (lights on at 06:00 h), and give standard laboratory chow and water ad libitum. Implant each rat with an intra-abdominal biotelimetry transmitter (Minnimitter-VMFH, series 4000, Sunriver, Oreg.) to monitor core body temperature and general activity. Implant each transmitter as per the manufacturer's recommendations under ketamine/xylazine (78/13 mg $kg^{-1}$, ip) general anesthesia and allow the animals to recover for 7-10 days. After the recovery period, to establish each animal's internal circadian cycle, place the animals in a constant dark cycle (0/24 h light/dark cycle) and allow the animals to go into free run for 7-10 days prior to test compound administration. During the dosing regimen, animals receive either vehicle or compound (ip, sc, or po) at specific CTs (Circadian Times) over a 48 hour period. Monitor the animals for 5 to 7 days in a constant dark cycle (0/24 h light/dark cycle) after completion of the dosing regimen. For each experiment, sample abdominal temperature and general activity data at 5-minute intervals. For analysis, use the Vital-View and Actiview software supplied by Minimitter. Plot observed abdominal temperatures obtained for each rat on the first day on a horizontal line. Align the line of observed abdominal temperatures below an abscissa line with circadian time (x-axis). Plot observed abdominal temperatures for each successive day as individual lines in a similar manner to provide the ordinate (y-axis, in days). Connect the initial rise of core body temperature that occurs each day with a straight line, which allows the use of multiple days to estimate the circadian phase on any given day for each individual rat. Determine the effect of treatment on phase by using the straight line multi-day estimation of phase before and after dosing. Treatment with an active compound will cause a greater displacement between the straight line connecting the daily initial rise of core body temperature before compound treatment and the straight line connecting the initial rise of core body temperature after compound treatment versus the vehicle control before and after treatment lines. Calculate the difference between those phases projected onto the day prior to dosing for the treated animals. Use ANOVA, together with Students t test, to compare mean body temperature circadian shifts in minutes between groups.

TABLE 5

Biological Data

| Cmpd No. | Casein Kinase Iε $^{33}$P-ATP Filter Plate Assay $K_i$ (nM) | Cell Assay $EC_{\Delta t1h}$ (μM) |
|---|---|---|
| Ia | 544 | |
| Ib | 157.35 | |
| Ic | >10⁴ | |
| Id | 110 | >30 |
| Ie | 159 | |
| If | 3090 | |
| Ig | 915.49 | |
| Ih | 70.95 | |
| Ii | 1677.81 | |
| Ij | 116.26 | |

TABLE 5-continued

Biological Data

| Cmpd No. | Casein Kinase Iε $^{33}$P-ATP Filter Plate Assay $K_i$ (nM) | Cell Assay $EC_{\Delta\tau 1h}$ (μM) |
|---|---|---|
| Ik | 468.28 | |
| Il | 324.03 | |
| Im | 1266.59 | |
| In | 237.97 | |
| Io | 78.65 | |
| Ip | 356.87 | |
| Iq | 37.99 | |
| Ir | 331.34 | |
| Is | 481.08 | |
| It | 425.30 | |
| Iu | 562 | |
| Iv | 4550.66 | |
| Iw | 2025.39 | |
| Ix | 1750.71 | |
| IIa | 64.04 | |
| IIb | 811 | 0.874 |
| IIc | 256.88 | |
| IId | 1067.73 | |
| IIe | 109.11 | |
| IIf | 1448.84 | |
| IIg | 30.64 | 2.492 |
| IIh | 24.73 | |
| IIi | — | |
| IIj | 112.37 | |
| IIk | 70.56 | |
| IIl | 184.63 | |
| IIm | 68 | |
| IIn | 15.90 | 0.998 |
| IIo | 9.60 | 0.662 |
| IIp | 4030 | |
| IIq | 334 | |
| IIr | 333 | |
| IIs | 47.00 | 1.155 |
| IIt | 22.00 | 1.974 |

6-(3-methoxyphenyl-sulfanyl)-4H-pyrrolo[3,2-d]thiazole-5-carboxylic acid amide.

What is claimed is:

1. A method for lengthening the circadian rhythm period in a patient through the inhibition of casein kinase Iε activity comprising administering to said patient a therapeutically effective amount of a compound of formula (I) or formula (II),

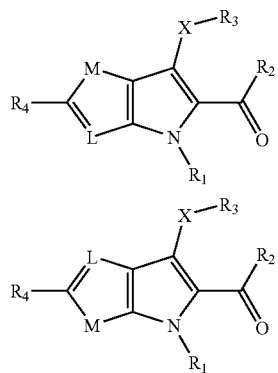

wherein
X is S or S(O)$_n$;
R$_1$ is H or C$_1$-C$_6$alkyl;
R$_2$ is NR$_5$R$_6$;
R$_3$ is aryl or heterocycle;
R$_4$ is H, C$_1$-C$_6$alkyl, C$_2$-C$_6$alkenyl, C$_2$-C$_6$alkynyl, aryl-(C$_1$-C$_6$alkyl), heterocycle-(C$_1$-C$_6$alkyl), C$_1$-C$_6$alkoxy, aryl-(C$_1$-C$_6$alkoxy), heterocycle-(C$_1$-C$_6$alkoxy), CF$_3$, halogen, SH, C$_{1-6}$alkylthio, aryl-(C$_1$-C$_6$alkylthio), heterocycle-(C$_1$-C$_6$alkylthio), NO$_2$, NH$_2$, NR$_5$R$_6$, aryl-(C$_1$-C$_6$alkylamino), heterocycle-(C$_1$-C$_6$alkylamino), or XR$_3$ wherein X and R$_3$ are as defined above;
R$_5$ is H or C$_1$-C$_6$alkyl;
R$_6$ is H or C$_1$-C$_6$alkyl;
L is N or CR$_7$ wherein R$_7$ is H or C$_1$-C$_6$alkyl;
M is S, O or NR$_8$ wherein R$_8$ is H, C$_1$-C$_6$alkyl, aryl-(C$_1$-C$_6$alkyl), heterocycle-(C$_1$-C$_6$alkyl) or acyl; and
n is 1 or 2; or
an enantiomer, tautomer or a racemates or a pharmaceutically acceptable salt thereof.

2. A method for treating a patient suffering from a sleep disorder ameliorated through the inhibition of casein kinase Iε activity comprising administering to said patient a therapeutically effective amount of a compound of formula (I) or formula (II),

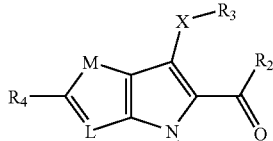

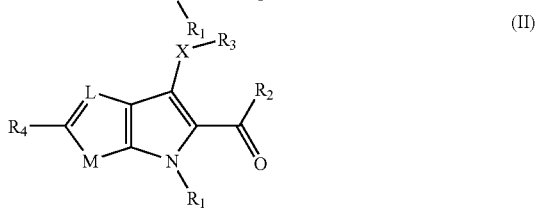

wherein
X is S or S(O)$_n$;
R$_1$ is H or C$_1$-C$_6$alkyl;
R$_2$ is NR$_5$R$_6$;
R$_3$ is aryl or heterocycle;
R$_4$ is H, C$_1$-C$_6$alkyl, C$_2$-C$_6$alkenyl, C$_2$-C$_6$alkynyl, aryl-(C$_1$-C$_6$alkyl), heterocycle-(C$_1$-C$_6$alkyl), C$_1$-C$_6$alkoxy, aryl-(C$_1$-C$_6$alkoxy), heterocycle-(C$_1$-C$_6$alkoxy), CF$_3$, halogen, SH, C$_{1-6}$alkylthio, aryl-(C$_1$-C$_6$alkylthio), heterocycle-(C$_1$-C$_6$alkylthio), NO$_2$, NH$_2$, NR$_5$R$_5$, aryl-(C$_1$-C$_6$alkylamino), heterocycle-(C$_1$-C$_6$alkylamino), or XR$_3$ wherein X and R$_3$ are as defined above;
R$_5$ is H or C$_1$-C$_6$alkyl;
R$_6$ is H or C$_1$-C$_6$alkyl;
L is N or CR$_7$ wherein R$_7$ is H or C$_1$-C$_6$alkyl;
M is S, O or NR$_8$ wherein R$_8$ is H, C$_1$-C$_6$alkyl, aryl-(C$_1$-C$_6$alkyl), heterocycle-(C$_1$-C$_6$alkyl) or acyl; and
n is 1 or 2; or an enantiomer, tautomer or a racemate or a pharmaceutically acceptable salt thereof.

3. The method of claim 2 wherein the sleep disorder is a circadian rhythm sleep disorder.

4. The method of claim 3 wherein the circadian rhythm sleep disorder is a shift work sleep disorder, jet lag syndrome, advanced sleep phase syndrome or a delayed sleep phase syndrome.

5. A method for treating a patient suffering from a sleep disorder ameliorated through the inhibition of casein kinase Iε activity comprising administering to said patient a therapeutically effective amount of a pharmaceutical composition comprising a pharmaceutically acceptable carrier and a compound of formula (I) or formula (II) as recited in claim 1 or an enantiomer, racemate, tautomer or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,652,046 B2 | Page 1 of 2 |
| APPLICATION NO. | : 12/125450 | |
| DATED | : January 26, 2010 | |
| INVENTOR(S) | : David Marc Fink et al. | |

It is certified that error appears in the above-identified patent and that said Letters Patent is hereby corrected as shown below:

On the first page, in field (60), in column 1, in "Related U.S. Application Data", line 5, delete "60/603,647," and insert -- 60/603,347, --, therefor.

On the first page, in field (56), in column 1, under "Other Publications", line 4, delete "www.nlm.nlh.gov/medlineplus/parkinsondisease.html" and insert -- www.nlm.nih.gov/medlineplus/parkinsondisease.html --, therefor.

In column 2, line 51, after "Nuclei" insert -- : --.

In column 20-21, line 33 and 1-2, delete " 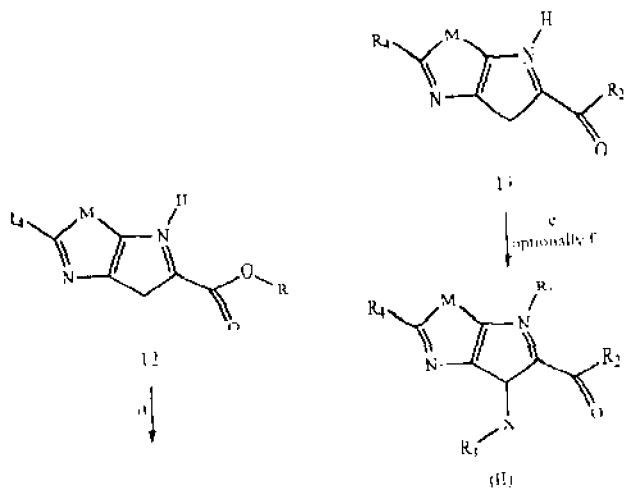 " and

Signed and Sealed this

Fifteenth Day of February, 2011

David J. Kappos
*Director of the United States Patent and Trademark Office*

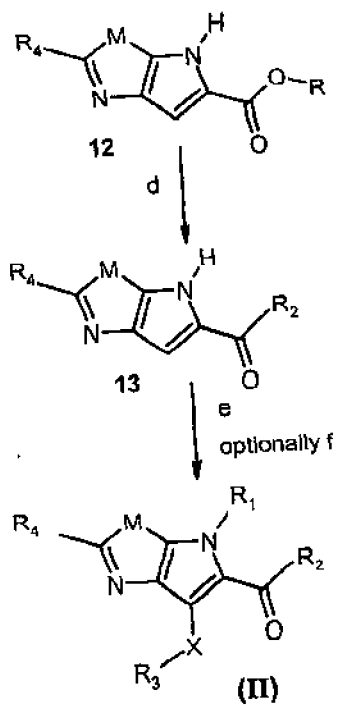
insert -- --.
In column 33, line 10, delete " 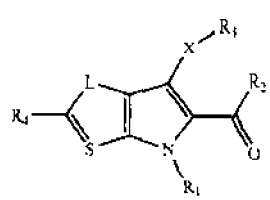 " and insert -- 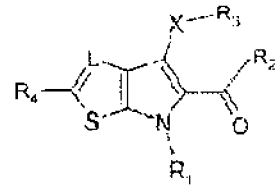 --, therefor.
In column 42, line 12, in claim 1, delete "racemates" and insert -- racemate --, therefor.
In column 42, line 42, in claim 2, delete "$NR_5R_5$," and insert -- $NR_5R_6$, --, therefor.